US011224757B2

(12) United States Patent
 Shang

(10) Patent No.: US 11,224,757 B2
(45) Date of Patent: *Jan. 18, 2022

(54) EXCHANGEABLE LASER UNIT AND ARRAY THEREOF

(71) Applicant: Hua Shang, Nanjing (CN)

(72) Inventor: Hua Shang, Nanjing (CN)

(73) Assignee: Hua Shang, Nanjing (CN)

( * ) Notice: Subject to any disclaimer, the term of this patent is extended or adjusted under 35 U.S.C. 154(b) by 18 days.

This patent is subject to a terminal disclaimer.

(21) Appl. No.: 16/756,814

(22) PCT Filed: Sep. 10, 2019

(86) PCT No.: PCT/CN2019/105135
§ 371 (c)(1),
(2) Date: Apr. 16, 2020

(87) PCT Pub. No.: WO2021/026999
PCT Pub. Date: Feb. 18, 2021

(65) Prior Publication Data
US 2021/0252300 A1    Aug. 19, 2021

(51) Int. Cl.
*A61N 5/06* (2006.01)
*H01S 5/02251* (2021.01)
(Continued)

(52) U.S. Cl.
CPC .............. *A61N 5/06* (2013.01); *A61N 5/062* (2013.01); *A61N 5/067* (2021.08);
(Continued)

(58) Field of Classification Search
CPC ......... B29D 30/02; B60B 31/005; B60B 9/26; B60C 7/18; B60C 7/24; B60C 2007/146;
(Continued)

(56) References Cited

U.S. PATENT DOCUMENTS

| 5,345,707 A | 9/1994 | Randall |
| 5,594,753 A | 1/1997 | Frey et al. |

(Continued)

FOREIGN PATENT DOCUMENTS

| CN | 201927886 U | 8/2011 |
| CN | 202678713 U | 1/2013 |

(Continued)

OTHER PUBLICATIONS

PCT International Search Report and Written Opinion, International Application No. PCT/CN2019/105135, dated May 39, 2020, 10 pages (Official copy and translation of search report).

(Continued)

*Primary Examiner* — Gary Jackson
*Assistant Examiner* — Sebastian X Lukjan
(74) *Attorney, Agent, or Firm* — AEON Law, PLLC; Adam L. K. Philipp; Shan Liao

(57) ABSTRACT

Disclosed is an exchangeable laser unit and an array thereof. The exchangeable laser unit includes cartridge receivers and housings having a uniform shape and uniform optical interfaces. The cartridge receiver adopts the optical interface including a tapered cavity and cylindrical cavity, so that a precise mechanical connection can be achieved between the output of laser of the cartridge receiver and the output of the optical fiber of the housing without professional tools, facilitating standardization of the output components of the laser elements of the cartridge receiver. In addition, the upper-lower guide rails and the upper-lower channels having certain of inclination degree can realize the precise positioning of the cartridge receiver and the housing. When replacing one laser element by a laser element that emits laser with a different wavelength, it is only necessary to replace the cartridge receiver inside the housing. That is, the replacement of laser elements having different wavelengths (Continued)

is converted to the replacement of cartridge receivers, which greatly reduces the difficulty for medical personnel to switch laser wavelengths, and improves the popularization of laser therapeutic instruments in the medical field. In the exchangeable laser array of the disclosure, the cartridge receiver inside the housing can be replaced by other cartridge receiver that emits laser with a different wavelength, and the plurality of housings can be connected with a plurality of wavelength switchers in the back to realize selective output of the wavelength.

9 Claims, 12 Drawing Sheets

(51) Int. Cl.
| | | |
|---|---|---|
| *A61N 5/067* | (2006.01) | |
| *H01S 3/02* | (2006.01) | |
| *H01S 3/03* | (2006.01) | |
| *H01S 3/04* | (2006.01) | |
| *H01S 3/041* | (2006.01) | |
| *H01S 3/042* | (2006.01) | |
| *H01S 5/024* | (2006.01) | |

(52) U.S. Cl.
CPC ............... *A61N 2005/063* (2013.01); *A61N 2005/0632* (2013.01); *H01S 3/025* (2013.01); *H01S 3/03* (2013.01); *H01S 3/041* (2013.01); *H01S 3/042* (2013.01); *H01S 3/0404* (2013.01); *H01S 3/0405* (2013.01); *H01S 5/02251* (2021.01); *H01S 5/02407* (2013.01); *H01S 5/02469* (2013.01)

(58) Field of Classification Search
CPC ....... B60C 7/14; B60C 7/26; A61N 2005/067; A61N 2005/0644; A61N 5/06; A61N 5/067; A61N 5/062; A61N 2005/063; A61N 2005/0632; A61B 18/22; A61B 5/062; H01S 6/02251; H01S 3/025; H01S 3/03; H01S 3/0404; H01S 3/0405; H01S 3/041; H01S 3/042; H01S 5/02407; H01S 5/02469; H01S 5/02; H01S 5/4087; H01S 5/005; H01S 3/23; H01S 5/40; H01S 5/022; G02B 6/42; G02B 6/4204
See application file for complete search history.

(56) References Cited

U.S. PATENT DOCUMENTS

| | | | |
|---|---|---|---|
| 10,918,881 B1* | 2/2021 | Shang | ................... H01S 3/2391 |
| 2004/0114858 A1 | 6/2004 | Komine | |
| 2013/0243377 A1 | 9/2013 | Seo et al. | |
| 2015/0306418 A1 | 10/2015 | Lee | |
| 2017/0353005 A1 | 12/2017 | Filgas et al. | |

FOREIGN PATENT DOCUMENTS

| | | |
|---|---|---|
| CN | 103953881 A | 7/2014 |
| CN | 203979998 U | 12/2014 |
| CN | 204411520 U | 6/2015 |
| CN | 206548602 U | 10/2017 |
| CN | 107703588 A | 2/2018 |
| CN | 110429455 A | 11/2019 |
| CN | 110445008 A | 11/2019 |
| KR | 101656227 B1 | 9/2016 |
| WO | 2016067343 A1 | 5/2016 |
| WO | 2016103643 A1 | 6/2016 |

OTHER PUBLICATIONS

The State Intellectual Property Office of People's Republic of China; First Office Action for Application No. 201910746084.6 dated Jun. 1, 2020, 11 pages.
The State Intellectual Property Office of People's Republic of China; Notification to Grant Patent Right for Invention for Application No. 201910746084.6 dated Jul. 6, 2020, 5 pages.

* cited by examiner

Multiple wavelength output by the plurality of optical fibers wavelength output by one optical fiber

EXCHANGEABLE LASER UNIT AND ARRAY THEREOF

CROSS-REFERENCE TO RELATED APPLICATIONS

This application is a U.S. national phase entry of PCT Application No. PCT/CN2019/105135 filed on Sep. 10, 2019, and naming "SHANG, Hua" as inventor and applicant, which claims priority to CN Patent Application No. CN201910746084.6 filed on Aug. 13, 2019. The above-cited applications are hereby incorporated by reference, in their entireties, for all purposes. The Application Data Sheet filed herewith forms a part of the present application, and all priority documents to which it refers are incorporated by reference herein in their entirety.

TECHNICAL FIELD

The present disclosure relates to the technical fields of laser and medical instruments, in particular relates to an exchangeable laser unit and an array thereof for photodynamic therapy.

BACKGROUND

Photodynamic Therapy (PDT) is a new technology for the diagnosis and treatment of diseases by using a photodynamic effect. This therapy is based on the photodynamic effect. The photodynamic effect belongs to a photosensitization reaction with biological effects in which oxygen molecule is involved, and comprises the following processes: a photosensitizer absorbed by a tissue is excited by the irradiation of a specific wavelength of laser; and then energies of the photosensitizer in the excited state are transferred to oxygen in the surrounding environment, to generate highly active singlet oxygen; the singlet oxygen and adjacent biomacromolecules occur oxidation reaction, and thus produce cytotoxicity, which in turn leads to cell damage or even death. Compared with traditional therapies, photodynamic therapy has many advantages including small trauma, good targeting, no drug resistance and side effects.

Laser is the most convenient and portable light source, and has coherence and mono-chromaticity. That is, a laser source can produce a single wavelength of light with the high energy. In addition, an output power of the laser source can be precisely regulated, and laser produced thereby can be directly introduced into hollow organs, penetrating into tumors through fiber optical cables. However, the lasers have a complicated structure, high price, and the use thereof is cumbersome. In addition, there is no sufficient training for medical personnel in the use of medical lasers, so that medical personnel feel fearful when using medical lasers, which seriously hinders the popularization of laser therapeutic instruments in the medical filed.

The photodynamic treatment time is related to the light absorbing ability of the photosensitizers and the effectiveness of energy transfer between light and oxygen. The laser wavelength and the required energy are variable depending on the indications being treated and the type of photosensitizer. Most of photosensitizers strongly absorb light with a wavelength of 630 nm or greater than 630 nm. For example, Photofrin is a photosensitizer used for gastric cancer and bladder cancer, and has an excitation wavelength of 630 nm; Metvix is a photosensitizer used for basal cell carcinoma, and has an excitation wavelength of 635 nm; Foscan is a photosensitizer used for head and neck tumors, and has an excitation wavelength of 652 nm; Purlytin is a photosensitizer used for breast cancer and prostate cancer, and has an excitation wavelength of 664 nm; Talaporfin is a broad spectrum photosensitizer used for solid tumors, and has an excitation wavelength of 664 nm; Verteporfin is a photosensitizer used for basal cell carcinoma, and has an excitation wavelength of 689 nm; Lutex is a photosensitizer used for prostate cancer and brain cancer, and has an excitation wavelength of 732 nm. For photodynamic therapy, there are many types of photosensitizers and applicable diseases, and new types of photosensitizers are constantly being introduced in the market. When replacing lasers or replacing the wavelength of laser, medical personnel who do not have common knowledge in the field of lasers are at a loss or prone to making mistakes.

For example, DIOMED 630 PDT Laser from Biolitec is a photodynamic laser dedicated to Photofrin, and has an emission wavelength of 630 nm; XD-635AB photodynamic laser treatment instrument manufactured by Guilin Xingda Company can emit laser with a wavelength of 635 nm, adopts optical output, and has an optical fiber core diameter of 400 μm. The above lasers can only emit laser with one wavelength. When the wavelength of laser needs to be changed, it is required to replace the bulk of the laser by professionals through using professional tools. In particular, the lasers used in the photodynamic therapy instruments are all semiconductor lasers which are output through optical fiber coupling. However, high coupling efficiency can only be achieved through a precise mechanical cooperation between the semiconductor laser and optical fiber coupling output interface and a precise mechanical cooperation between optical fiber and optical fiber coupling output port. In addition, it is difficult to quickly and accurately align the bulk of laser body and the related interfaces when replacing the laser.

SUMMARY

In view of the above, an object of the present disclosure is to provide an exchangeable laser unit capable of quickly and accurately switching laser elements, and an array thereof.

An exchangeable laser unit is provided. The exchangeable laser unit includes laser elements, and further includes cartridge receivers for fixing the laser elements and a housing for clamping the cartridge receivers. The housing is used for clamping with a plurality of cartridge receivers having same shape. The cartridge receivers have same shape and optical interface. The housing is provided with one optical joint for matching with the optical interface of the cartridge receiver. The optical interface includes a tapered cavity with a cone top at front and an axis extending rearward. A small cylindrical cavity is arranged extending horizontally forwardly from the cone top of the tapered cavity and is communication with the tapered cavity; a big cylindrical cavity is arranged extending horizontally backwardly from a cone bottom of the tapered cavity. A front side of the small cylindrical cavity is directly connected a laser output of the laser element, or is connected to the laser output of the laser element through an optical fiber ferrule. The optical joint capable of matching with the optical interface of the cartridge receiver is provided on a back panel of the housing. The optical joint includes a tapered adapter having a same shape as the tapered cavity, and an external optical fiber disposed at axes position of the tapered adapter. A front end of the external optical fiber is provided with an external optical fiber ferrule capable of inserting into the small cylindrical cavity. The external optical fiber ferrule is arranged at a front end of the tapered adapter, a cylindrical adapter with a same shape as the large cylindrical cavity is arranged extending forwardly from a back end of the tapered adapter. The cylindrical adapter extends to the back panel of the housing and to be flush with the back panel of the housing.

The housing includes a first accommodating space for accommodating the cartridge receiver. A front panel of the housing is provided with an insertion port for a horizontal insertion of the cartridge receiver into the first accommodating space. The first accommodating space and the cartridge receiver have a same shape. A left panel and a right panel of the cartridge receiver are provided with horizontal positioning grooves, and a left panel and a right panel of the first accommodating space cartridge receiver are provided correspondingly with horizontal positioning protrusions. The housing further includes a clamping unit and a second accommodating space for accommodating the clamping unit. The second accommodating space is disposed under the first accommodating space and is communication with the first accommodating space through a clamping port provided on a bottom panel of the first accommodating space. The clamping unit includes a clip-lock assembly, and the clip-lock assembly includes a clip-lock panel disposed horizontally and an elastic assembly disposed under the clip-lock panel.

The clamping unit further includes a clamping box, and the clamping box is fixed to the second accommodating space. A lower portion of the elastic assembly is fixed to a bottom of the clamping box. A left side and right side of the clamping box are provided with a plurality of backwardly inclined upper-lower guide rails, and a left and right sides of the clip-lock panel are correspondingly provided with a plurality of backwardly inclined upper-lower guide channels. The clip-lock panel can be moved upward under an action of the elastic assembly, and an upper and lower position of the optical interface can be accurately positioned, so that the external optical fiber ferrule is accurately docked with the small cylindrical cavity when the cartridge receiver is pushed into the first accommodating space.

An exchangeable laser array is provided. The exchangeable laser array includes at least two of the above-mentioned exchangeable laser units, and in each of exchangeable laser units, a left side and right side of the housing are respectively provided with a horizontal guide channel array and a horizontal guide rail array.

Preferably, the exchangeable laser array further includes a wavelength switcher. The wavelength switcher includes a plurality of optical fiber input interfaces connected (directly or indirectly) to optical interfaces of exchangeable laser units of the exchangeable laser array, one optical fiber output interface, a base and a plurality of optical fiber plugs. The base includes a baseplate and a stationary shaft extending upward along a center of the baseplate. The stationary shaft is fixed with a drive gear and an optical fiber displacement disk that coincide with an axis of the stationary shaft from bottom to top. The optical fiber plugs include optical fiber plugging rods, a driven gear assembly disposed at periphery of the optical fiber plugging rods and meshing with the drive gear. One end of the optical fiber plugging rod is connected to the optical fiber input interface, and other end of the optical fiber plugging rod is actively connected to the optical fiber output interface. Preferably, a plurality of optical fiber plugging ports for positioning the optical fiber plugs are axisymmetrically disposed on the optical fiber displacement disk at a radial periphery of the drive gear. A plurality of output ports for spirally connecting the optical fiber output interfaces are disposed on the baseplate vertically corresponding to the optical fiber plugging ports.

Preferably, when the optical fiber plugging rods are located above the baseplate, the optical fiber displacement disk is rotated under an action of the drive gear and driven gear; when the optical fiber plugging rod is rotated to locate above the output port, the optical fiber plugging rods is moved up or down along the optical fiber plugging port under the action of the drive gear and driven gear, so as to pull out from the output port or insert into the optical fiber output port.

Preferably, the wavelength switcher further includes a micro-switch device disposed above the optical fiber displacement disk. The micro-switch device includes a micro-switchgear, and a plurality of micro-switch elements. Micro-switch positioning slots with the same angle as the optical fiber plugs are disposed on the optical fiber displacement disk. When the optical fiber displacement disk is rotated, a triggering unit of the micro-switch elements moves from one micro-switch positioning slot to an adjacent micro-switch positioning slot. At the same time, the optical fiber plug is moved from an upper position of one output port to an upper position of an adjacent output port. Specifically, the optical fiber plugging ports are axisymmetrically disposed on the optical fiber displacement disk, and micro-switch positioning slots are adaptively disposed in a radial direction of the fiber displacement disk in which the optical fiber plugging ports are located, so as to ensure that the optical fiber plug can be accurately positioned above the output ports when the optical fiber displacement disk is rotated.

Preferably, the driven gear is connected to the optical fiber plugging rods through a screw-nut pair. On the optical fiber plugging rods, lower portions of the optical fiber plugging rods are provided with vertical positioning slots matching with positioning protrusions of the optical fiber plugging ports. Upper portions of the vertical positioning slots are provided with a screw external thread matching with a screw internal thread of the driven gear.

Preferably, the screw internal thread of the driven gear is longer than the screw external thread of the optical fiber plugging rod. When a top of the screw external thread abuts against a top of the screw internal thread, and/or when a bottom of the vertical positioning slot abuts against a bottom of the positioning protrusion, a bottom of the optical fiber plugging rod is located at least above the baseplate.

The present disclosure has the following advantages.

1. The exchangeable laser unit of the disclosure is composed of cartridge receivers having a uniform shape, a uniform optical interface and including laser elements inside thereof and a housing for clamping the cartridge receivers. The laser elements inside the cartridge receivers may be a semiconductor laser element, a solid laser element, a gas laser element or other kinds of laser elements. Laser is output through the same optical joint provided at the back panel of the housing. The cartridge receiver adopts an optical interface with a tapered cavity and a cylindrical cavity, and an optical joint matching with said optical interface is provided with a tapered adapter and cylindrical adapter, so that a precise mechanical connection can be achieved between the output of the laser elements of the cartridge receiver and the output of the optical fiber of the housing without professional tools, facilitating standardization of the output components of the laser elements of the cartridge receiver. In addition, the upper-lower guide rails and the upper-lower channels having certain of inclination degree can realize the precise positioning of the cartridge receiver and the housing. When replacing one laser element by a laser element that emits laser with a different wavelength, it is only necessary to withdraw the current cartridge receiver from the housing, and replace it by another cartridge receiver that includes the laser element emitting laser with the different wavelength. Therefore, the replacement of laser elements is converted to the replacement of cartridge receivers that include different laser elements emitting laser with different wavelengths, and have uniform shapes, uniform optical interfaces, which greatly reduces the difficulty for medical personnel to switch laser wavelengths, and improves the popularization of laser therapeutic instruments in the medical field.

2. According to the exchangeable laser unit of the disclosure, the power supply and parameter controls of the laser element are realized by cylindrical protrusions with a certain degree of inclination on clip-lock panel and electronic interfaces within cylindrical slots of the cartridge receiver. In addition, the cylindrical protrusions and cylindrical slots with the certain degree of inclination can realize precise positioning of the cartridge receiver and the housing.

3. According to the exchangeable laser unit of the disclosure, the clip-lock panels include mechanical buckles. The buckle is engaged with the buckle slot of the cartridge receiver to further prevent the cartridge receiver from coming out of the housing. This improves the security and stability of the system. In addition, the cartridge receiver has the anti-slip groove structure, which is convenient for the user to remove the cartridge receiver from the first accommodating space or insert the cartridge receiver into the first accommodating space of the housing, thereby laying a foundation for the extensive use in the medical field.

4. In the exchangeable laser array of the disclosure, housings have uniform optical fiber joints and electronic joints. The optical fiber joints of the housings are directly or indirectly connected to external optical fibers, and output lasers having multiple wavelengths, and output through different optical fibers to different instruments such as photodynamic therapy devices or dedicated wavelength switchers. When the photosensitizer needs to be replaced temporary during the treatment, it is only necessary to purchase a cartridge receiver that corresponds to the wavelength of the photosensitizer and insert it into the housing.

5. In the exchangeable laser array of the disclosure, the cartridge receiver inside the housing can be replaced by other cartridge receiver that emits laser with a different wavelength. The housings may be connected with wavelength switchers to realize selective output of the wavelength.

LIST OF REFERENCE SYMBOLS 1, cartridge receiver; 11, electrical interface; 12, optical interface; 121, tapered cavity; 122, small cylindrical cavity; 123, large cylindrical cavity; 124, optical fiber ferrule; 125, convex lens; 13, cylindrical slot; 14, buckle slot; 15, heat sink; 151, cooling inlet for heat sink; 16, horizontal positioning groove; 17, anti-slip groove structure; 18, display device; 2, housing; 21, first accommodating space; 211, insertion port; 2111, plugging cartridge receiver groove; 212, clamping port; 213, horizontal positioning protrusion; 22, clamping unit; 221, clip-lock assembly; 2211, clip-lock panel; 22111, upper-lower guide channels; 22112, inclined strip-shaped groove; 2212, elastic assembly; 222, button assembly; 2221, release button; 2221a, vertical strip-shaped groove; 2222, frame connector; 22221, upper rod; 22222, lower rod; 22223, left rod; 22224, right rod; 223, clamping box; 2231, upper-lower guide rails; 23, second accommodating space; 24, cylindrical protrusion; 25, optical joint; 251, tapered adapter; 252, external optical fiber; 253, external optical fiber ferrule; 254, cylindrical adapter; 26, buckle; 27, forced air cooling inlet; 28, forced air cooling outlet; 29, electrical input joint; 3, wavelength switcher; 31, optical fiber input interface; 32, optical fiber output interface; 33, base; 331, baseplate; 3311, output port; 332, stationary shaft; 34, optical fiber plug; 341, optical fiber plugging rod; 3411, vertical positioning groove; 342, driven gear, 3421, screw-nut pair; 3422, optical fiber plugging rod bearing; 343, spring; 344, spring positioning shoulder; 35, drive gear; 36, optical fiber displacement disk; 361, optical fiber plugging port; 362, micro-switch positioning slot; 37, micro-switch device; 371, micro-switchgear; 3711, micro-slot; 372, micro-switch element; 373, micro-motion spring; 374, limiting ball; 375, micro-motion rod

DETAILED DESCRIPTION

Reference will now be made in detail to exemplary embodiments, examples of which are illustrated in the accompanying drawings, in order to facilitate the understanding of the disclosure. The following description and the accompanying drawings only show preferred examples, and the disclosure may be embodied in many different forms and not limited to the examples described herein. Rather, these examples are provided for fully understanding of the present disclosure. In particular, the directional terms used in the disclosure, such as "upper", "lower", "before", "after", "left", "right", "inside", "outside", "side" are only referred to the orientation in accompanying drawings. It should be understand that the directional terms are used to illustrate the disclosure, and are not intended to limit the disclosure.

Example 1

Figure 10:
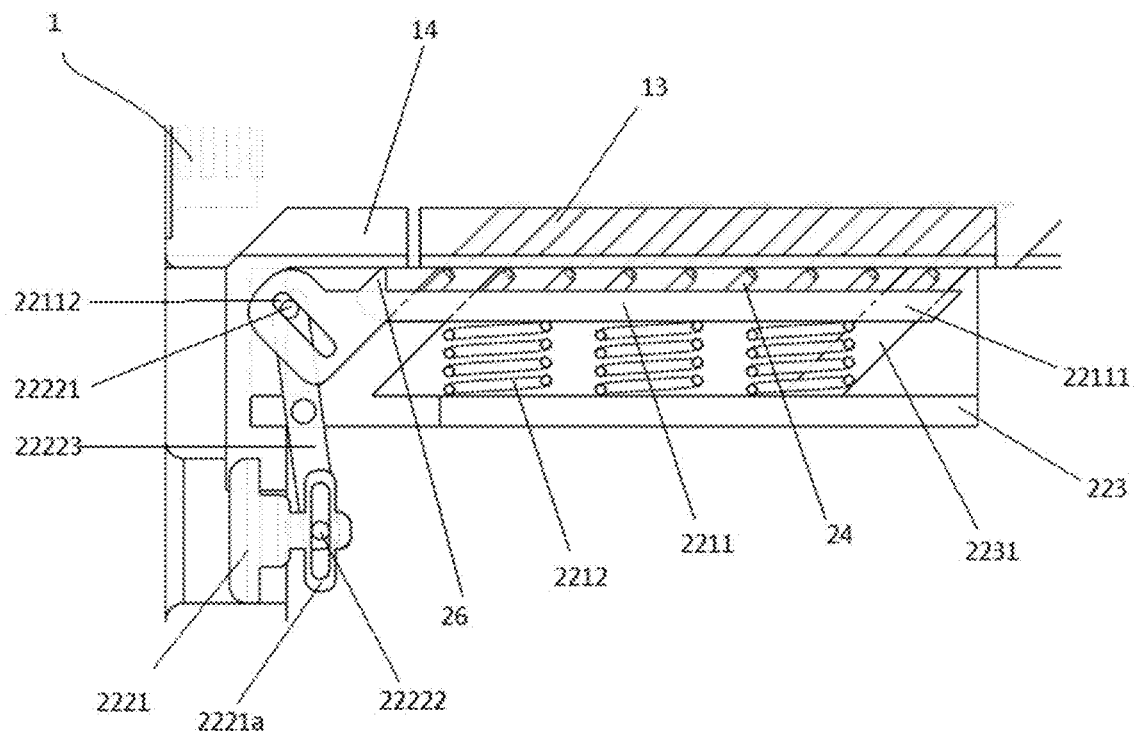
FIG. 10 is a schematic diagram illustrating the structure of the exchangeable laser unit according to example 2 of the disclosure in which the clamping unit is not clamped to the cartridge receiver.
Figure 11:
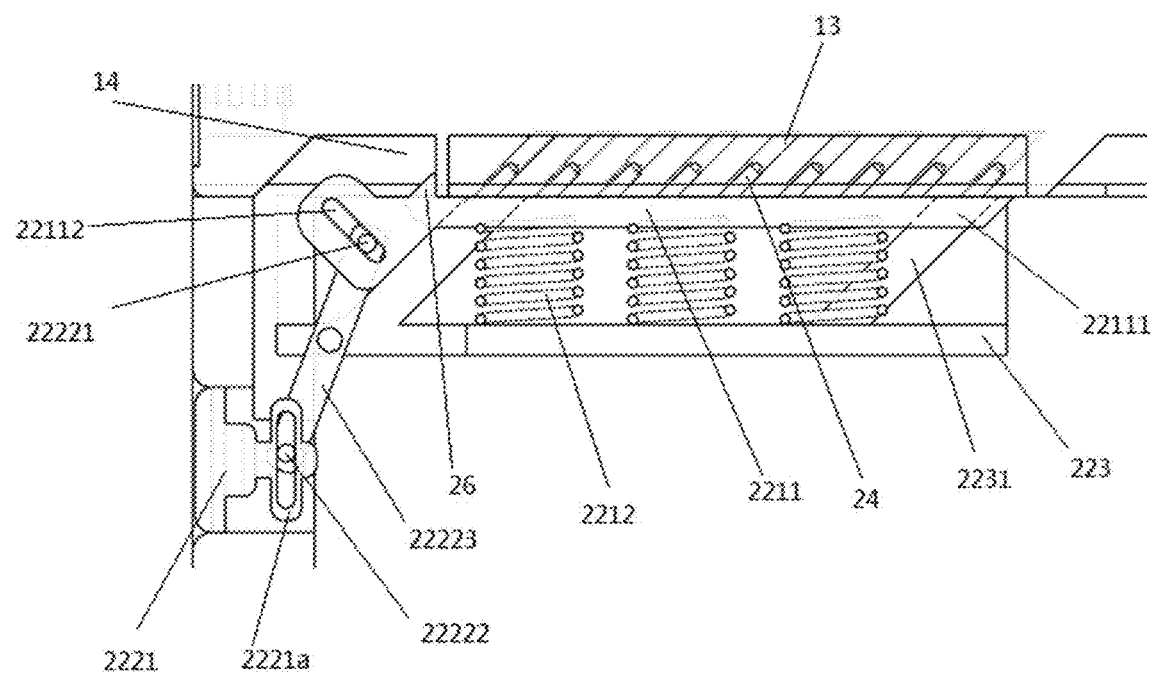
FIG. 11 is a schematic diagram illustrating the structure of the exchangeable laser unit according to example 2 of the disclosure in which the clamping unit is clamped to the cartridge receiver.
Figure 12:
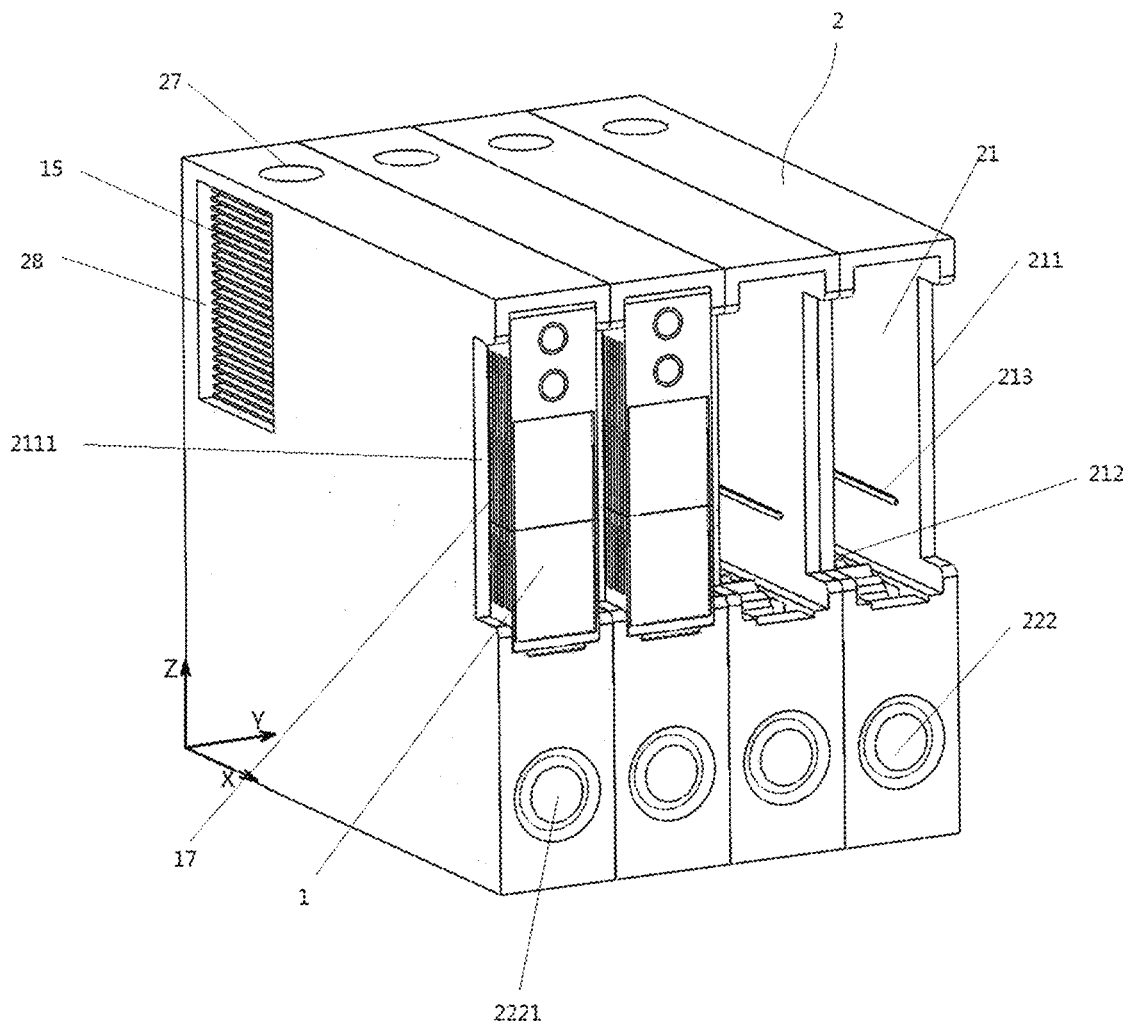
FIG. 12 is a three-dimensional schematic diagram illustrating the structure of the exchangeable laser array of the disclosure.

As shown in FIGS. 1-12, an exchangeable laser unit is provided. The exchangeable laser unit includes a cartridge receiver 1 in which a laser element is fixed and a housing 2 for clamping the cartridge receiver 1. The cartridge receiver 1 has one electrical interface 11 and several optical interfaces 12 for docking with the housing 2. The cartridge receiver 1 can be withdrawn from the housing 2 and replaced by another cartridge receiver including a laser element that emits laser of different wavelength. Since there are many drawings in the disclosure, the word "front" refers to the position of the insertion port when the cartridge receiver is inserted into the housing in FIGS. 1-12 for the unified identification. That is, the position of the front panel of the housing is referred as "front", and the position of the back panel of the housing opposite thereto is referred as "back". Specifically, the coordinate system in FIG. 12 is that the direction indicated by the X-axis is referred as "front", the direction indicated by the Y-axis is referred as "right", and the direction indicated by the Z-axis is referred as "upper".

Specifically, the housing 2 includes a first accommodating space 21 for accommodating the cartridge receiver 1, a clamping unit 22, and a second accommodating space 23 for accommodating the clamping unit. A front panel of the housing 2 is provided with an insertion port 211 for horizontally inserting the cartridge receiver 1 into the first accommodating space 21. The cartridge receiver 1 is detached and replaced via the insertion port 211. The second accommodating space 23 is disposed below the first accommodating space 21 and is communication with the first accommodating space 21 through a clamping port 212 provided on a bottom panel of the first accommodating space 21.

Preferably, a back panel of the housing 2 is provided with an optical joint 25 at a position of the back panel horizontally corresponding to the insertion port 211, and the cartridge receiver 1 is provided with an optical interface 12 for matching the optical joint at a position corresponding to the optical joint. The optical interface 12 is internally connected to a laser output port of the cartridge receiver via optical fibers. Different cartridge receivers are designed to have uniform optical interfaces 12 and electrical interface 11, which greatly reduces the difficulty for medical personnel to switch laser wavelengths, and improves the popularization of laser therapeutic instruments in the medical field.

Figure 5:
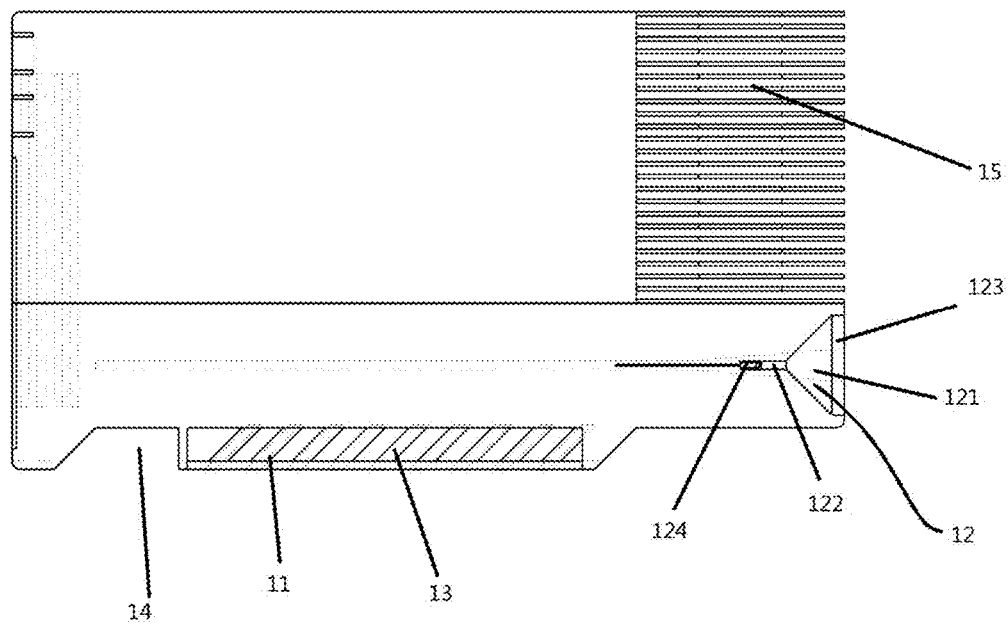
FIG. 5 is a cross-sectional schematic diagram film the right view illustrating the structure of the cartridge receiver of the exchangeable laser unit according to example 1 of the disclosure.
Figure 6:
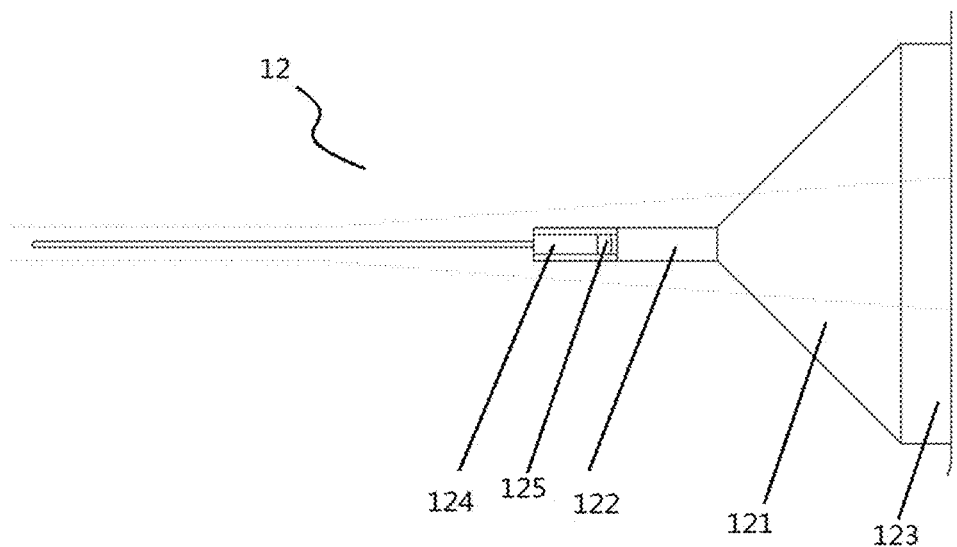
FIG. 6 is a schematic diagram from the right view illustrating the optical interface of the exchangeable laser unit according to example 1 of the disclosure.

In particular, as shown in FIGS. 5-6, the optical interface 12 of the cartridge receiver 1 includes a tapered cavity 121 with a cone top at front and an axis extending rearward. A small cylindrical cavity 122 is arranged extending horizontally forward from the cone top of the tapered cavity 121 and is communication with the tapered cavity. A big cylindrical cavity 123 is arranged extending horizontally backward from a cone bottom of the tapered cavity 121. A front side of the small cylindrical cavity 122 is directly connected a laser output port of the laser element, or connected to the laser output port of the laser element through an optical fiber fermule 124.

Figure 2:
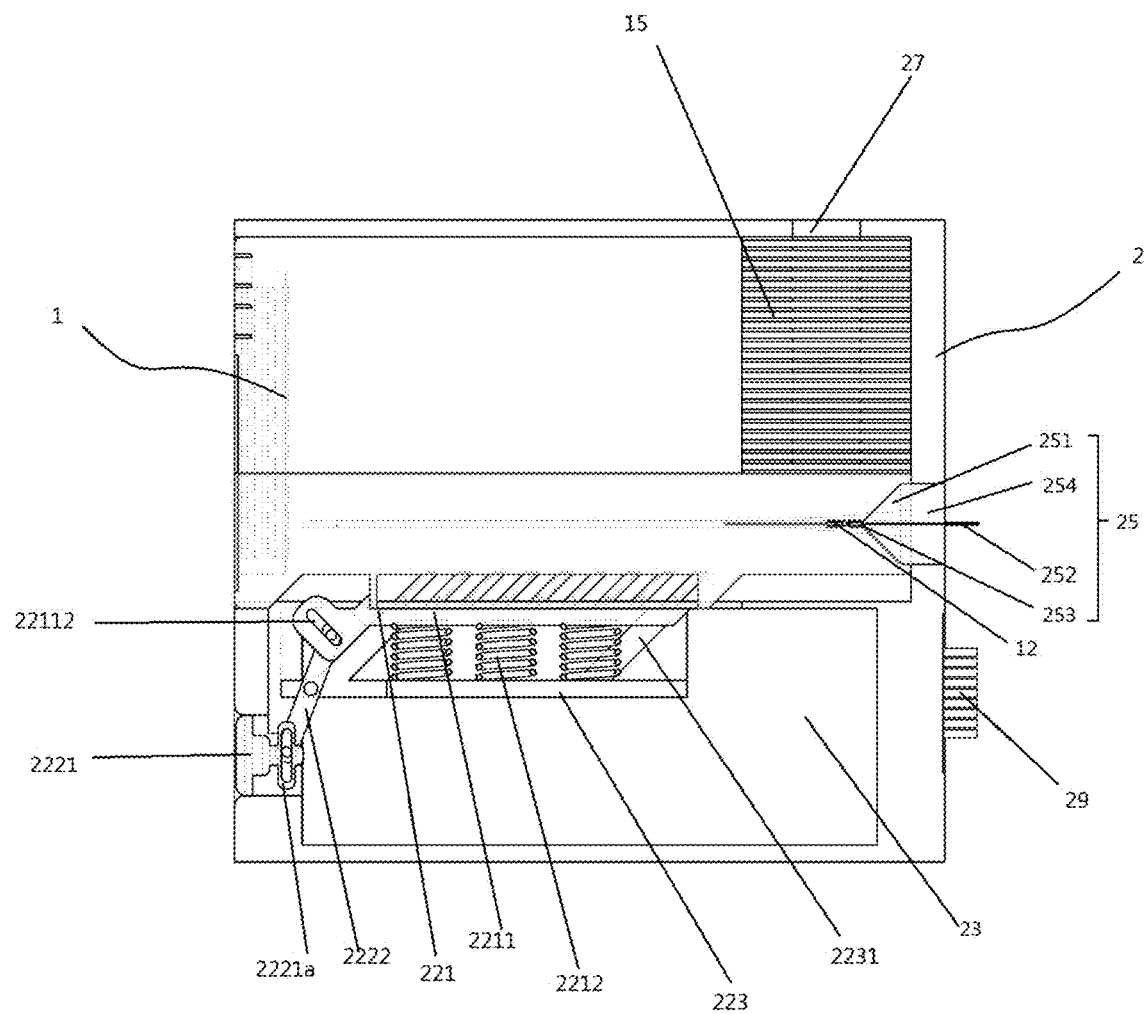
FIG. 2 is a three-dimensional schematic diagram illustrating the structure of the exchangeable laser unit according to example 1 of the disclosure.
Figure 7:
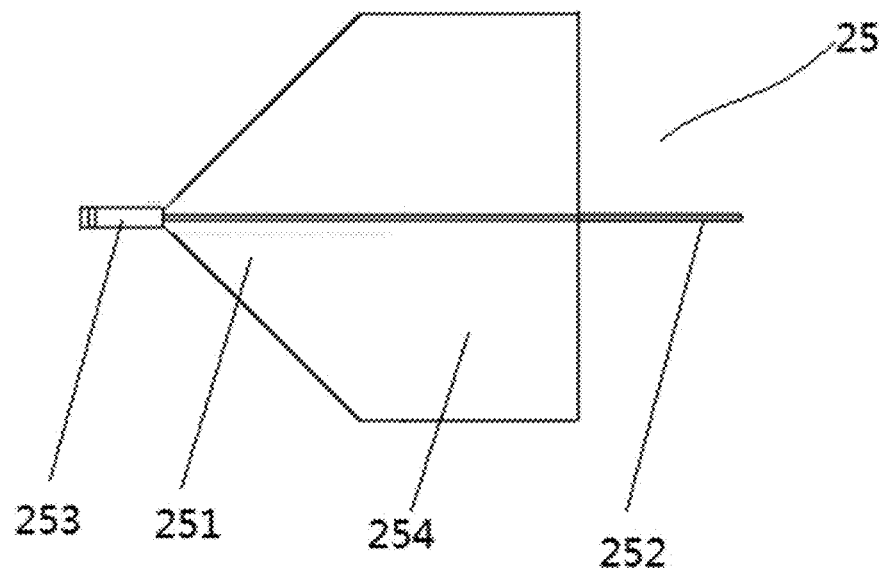
FIG. 7 is a schematic diagram from the right view illustrating the optical joint of the exchangeable laser unit according to example 1 of the disclosure.

The back panel of the housing 2 is provided with an optical joint 25 (i.e., an optical connector) capable of matching with the optical interface of the cartridge receiver. As shown in FIGS. 2 and 7, the optical joint 25 includes a tapered adapter 251 having the same shape as the tapered cavity 121, and an external optical fiber 252 disposed inside the tapered adapter 251. A front end of the external optical fiber 252 is provided with an external optical fiber ferrule 253 capable of inserting into the small cylindrical cavity 122. The external optical fiber ferrule 253 is arranged at a front end of the tapered adapter 251, and a cylindrical adapter 254 with the same shape as the large cylindrical cavity 123 is arranged extending forwardly from a back end of the tapered adapter 251. The cylindrical adapter 254 may extend to be flush with the back panel of the housing 2.

Figure 8:
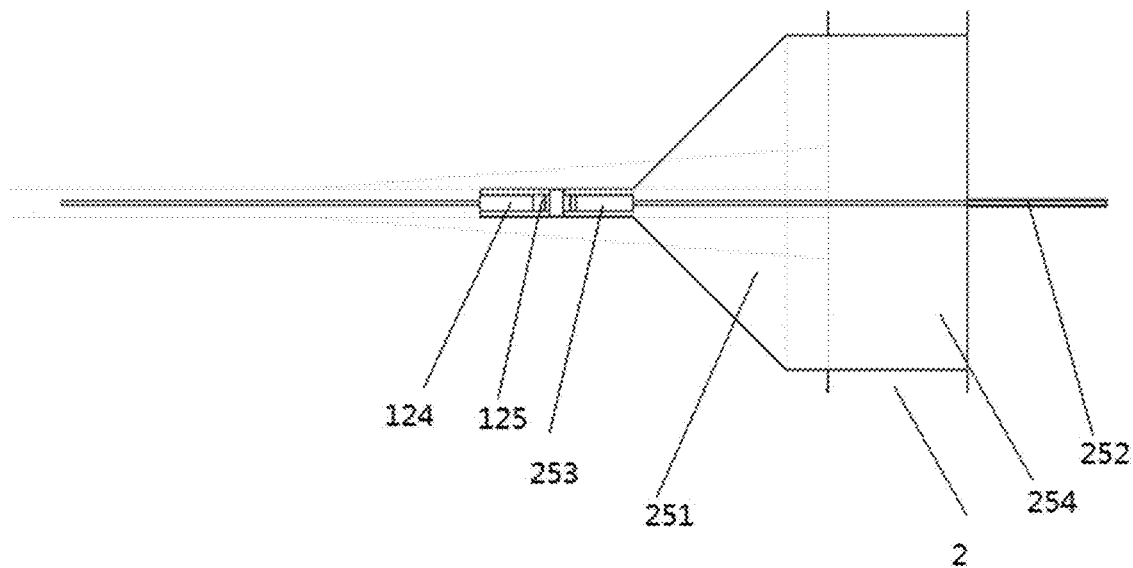
FIG. 8 is a schematic diagram illustrating the assembly structure of the optical interface and the optical joint of the exchangeable laser unit according to example 1 of the disclosure.

A top portion of the optical fiber ferrule 124 has a lens 125, and the lens is a convex lens or a lenticular lens or a graded-index lens. When the optical interface 12 is mated with the optical joint 25, a distance between a front end face of an optical fiber of the external optical fiber ferrule 253 and the lens is equal to a focal length of the lens, or half of it or an integral multiple thereof, collimating the divergent light emitting from the optical fiber. In this example, a core diameter of the optical fiber is 400 μm, and the optical fiber ferrule 124 has a diameter of 3 mm, and the lens is a convex lens 125. The small cylindrical cavity 122 allows the insertion of the external optical fiber ferrule 253. The assembly structure of the optical interface 12 and the optical joint 25 is shown in FIG. 8. The optical fiber ferrule 124 of the laser element outputs laser in a collimated manner, and is coupled with the external optical fiber ferrule 253 inside the housing 2, so as to output laser through the external optical fiber 252. There is a gap between the top end of the optical fiber ferrule 124 of the laser element and the top end of the external optical fiber ferrule 253 of the housing 2, preventing the top end of the optical fiber ferrule 124 and the top end of the external optical fiber ferrule 253 from being damaged by the external force collision. The gap may be in a size of 10 μm-1000 μm. In this example, this gap is 500 μm.

Preferably, the tapered cavity has a taper angle of 45°. The arrangement of the tapered adapter 251 and the tapered cavity 121 having the taper angle of 45° as well as the mechanical structures of the large cylindrical cavity 123 and the cylindrical adapter 254, enable the optical fiber ferrule 124 of the laser element and the external optical fiber ferrule 253 can be precisely docked with each other.

Figure 1:
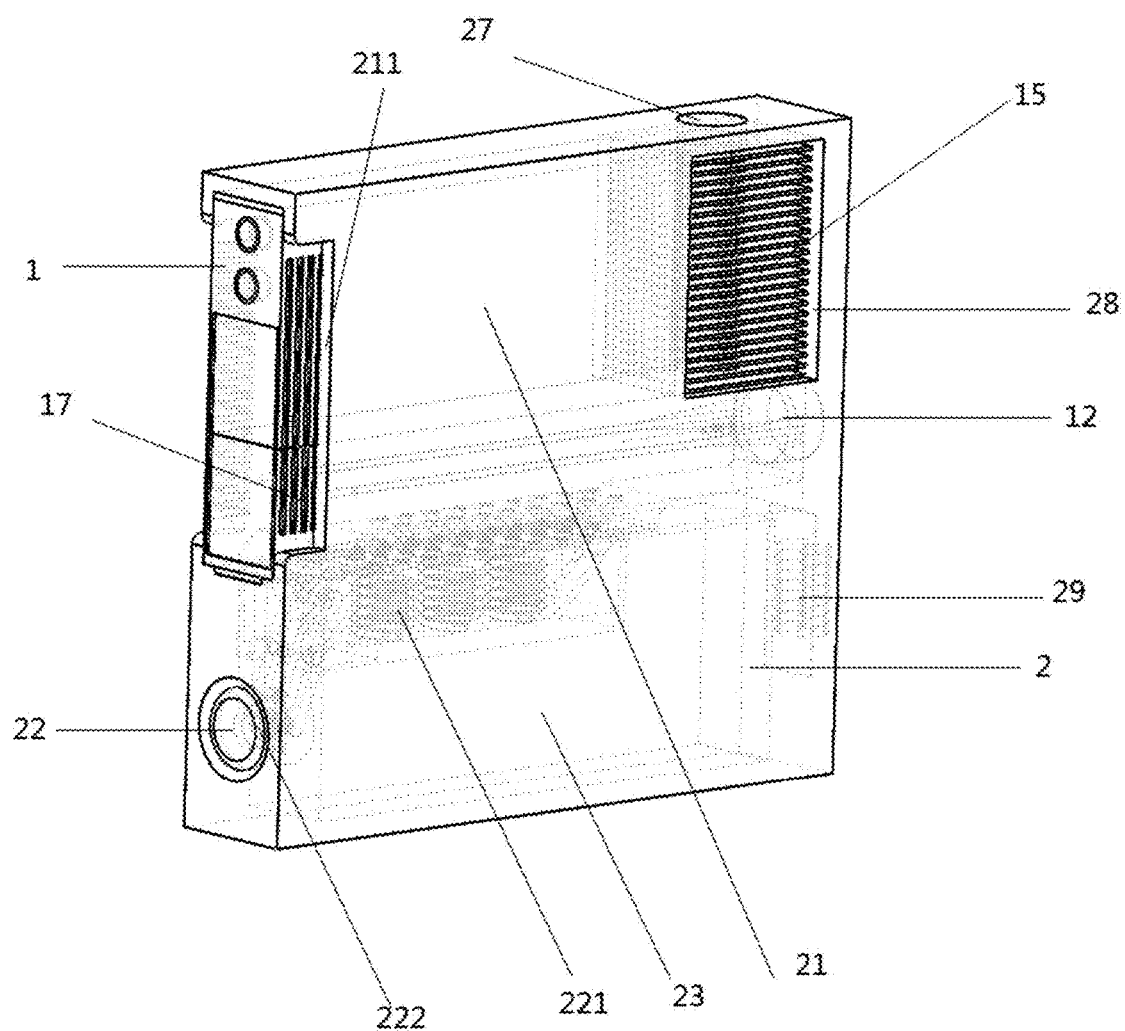
FIG. 1 is a cross-sectional schematic diagram from the right view illustrating the exchangeable laser unit according to example 1 of the disclosure.
Figure 3:
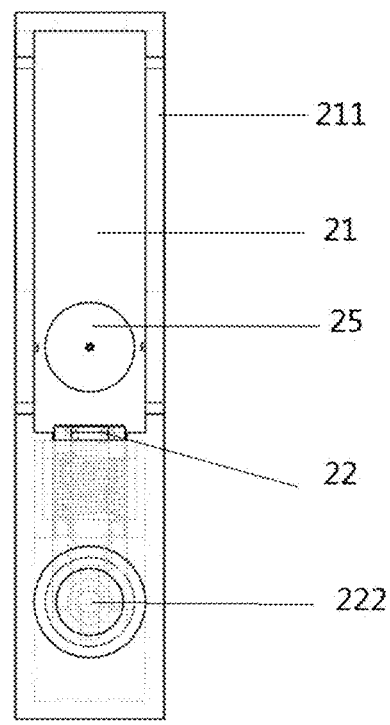
FIG. 3 is a schematic diagram from the front view illustrating the structure of the exchangeable laser unit according to example 1 of the disclosure.
Figure 4:
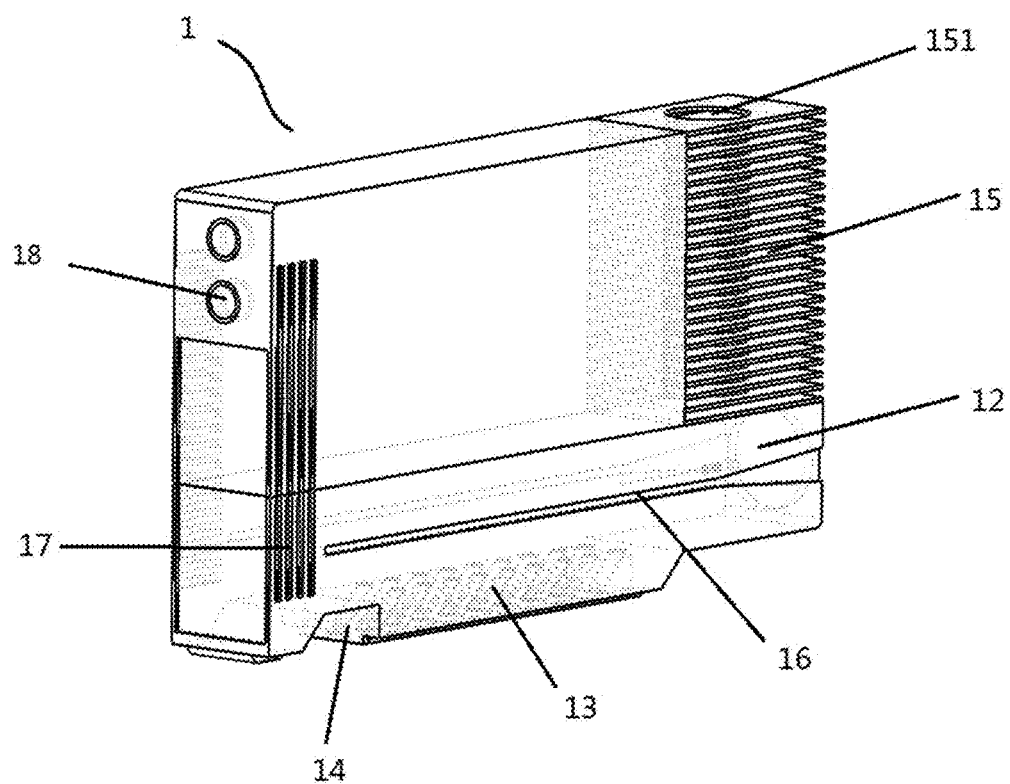
FIG. 4 is a three-dimensional schematic diagram illustrating the structure of the cartridge receiver of the exchangeable laser unit according to example 1 of the disclosure.

FIGS. 1-3 show the structure of the cartridge receiver 1 when it is not inserted into the housing 2. Preferably, the first accommodating space 21 and the cartridge receiver 1 have a same shape. The left panel and the right panel of the cartridge receiver 1 are provided with horizontal positioning grooves 16, and the left panel and the right panel of the first accommodating space 21 corresponding to the left panel and the right panel of the cartridge receiver 1 are provided with horizontal positioning protrusions 213.

Figure 9:
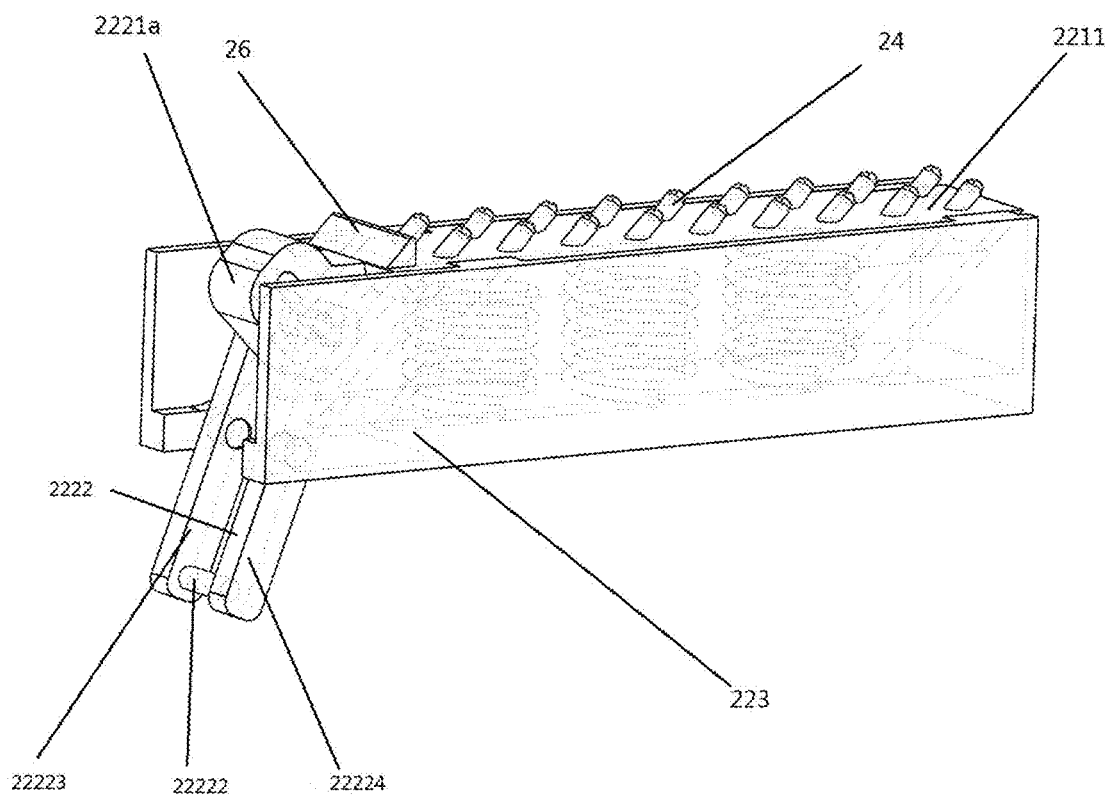
FIG. 9 is a three-dimensional schematic diagram illustrating the structure of the clamping unit of the exchangeable laser unit according to example 2 of the disclosure.

In order to realize the precise positioning of optical interfaces between the housing 2 and the cartridge receiver 1, as shown in FIGS. 9-11. The clamping unit 22 includes a clip-lock assembly 221. The clip-lock assembly 221 includes a clip-lock panel 2211 disposed horizontally and an elastic assembly 2212 disposed under the clip-lock panel. The clamping unit 22 further includes a clamping box 223. The clamping box 223 is fixed to the second accommodating space 23. In addition, a lower portion of the elastic assembly 2212 is fixed to a bottom of the clamping box 223. When the clip-lock panel 2211 is moved up and down under the action of the elastic assembly 2212, the clip-lock panel is not completely detached from the clamping box 223. A left and right sides of the clamping box 223 are respectively provided with a plurality of upper-lower guide rails 2231, and a left and right sides of the clip-lock panel 2211 corresponding to the clamping box are provided with upper-lower guide channels 22111 respectively. Alternatively, the left and right side surfaces of the second accommodating space 23 are preferably provided with a plurality of backwardly inclined upper-lower guide rails 2231, and left and right sides of the clip-lock panel 2211 corresponding to the second accommodating space are provided with upper-lower guide channels 22111. In addition, the lower portion of the elastic assembly 2212 is fixed to a bottom of the second accommodating space 23. When the clip-lock panel 2211 is moved up and down, the clip-lock panel is not completely detached from the upper-lower guide rails.

The exchangeable laser unit of the disclosure is composed of cartridge receivers 1 having a uniform shape, a uniform electrical interface 11 and uniform optical interface 12 and including laser elements inside thereof and a housing 2 for clamping the cartridge receivers 1. The laser element inside the cartridge receiver 1 may be a semiconductor laser element, a solid laser element, a gas laser element or other kinds of laser elements. Laser is output through the same optical joint 25 provided at the back of the housing 2. The cartridge receiver adopts an optical interface with a tapered cavity and a cylindrical cavity, and an optical joint matching with this optical interface is provided with a tapered adapter and cylindrical adapter, so that a precise mechanical connection can be achieved between the output of the laser elements of the cartridge receiver and the output of the optical fiber of the housing without professional tools, facilitating standardization of the output components of the laser elements of the cartridge receiver. The upper-lower guide rails and the upper-lower channels can realize the precise positioning of the cartridge receiver 1 and the housing 2. When replacing one laser element by a laser element that emits laser with a different wavelength, it is only necessary to withdraw the current cartridge receiver 1 from the housing 2, and replace it by another cartridge receiver that includes the laser element emitting laser with a different wavelength. That is, the replacement of laser elements is converted to the replacement of cartridge receivers 1 that include different laser elements emitting laser with different wavelengths, and have uniform shapes, uniform optical interfaces, which greatly reduces the difficulty for medical personnel to switch laser wavelengths, and improves the popularization of laser therapeutic instruments in the medical field.

Example 2

Preferably, this example differs from the above example in that: as shown in FIGS. 1-11, an upper panel of the clip-lock panel 2211 is provided with a plurality of cylindrical protrusions 24 whose axes are inclined rearward, and a corresponding lower panel of the cartridge receiver 1 is provided with a plurality of cylindrical slots 13 having the same shape as the cylindrical protrusions 24. The cylindrical protrusions 24 pass upward through the clamping port 212 and snap into the cylindrical slots 13 under an action of the elastic assembly 2212.

Preferably, the clamping unit 22 further includes a button assembly 222. When the button assembly 222 moves backward, the clip-lock panel 2211 is driven to move obliquely downward along an axial direction of the cylindrical protrusion 24, the elastic assembly 2212 is switched from a natural state to an energy storage state, and the cylindrical protrusions disengage from the cylindrical slots 13, thereby causing the cartridge receiver 1 to be disengaged from the clip-lock panel 2211. This facilitates the withdrawal of the cartridge receiver 1 from the insertion port 211 and the arrangement of other cartridge receiver having the same structure but including a different laser element that emits laser of different wavelength. That is, the switching of the wavelength of the laser can be completed by simply switching the cartridge receiver 1. When the other cartridge receiver is arranged into the first accommodating space 21 and the button assembly 222 is released (the button assembly 222 is reset forward), the elastic assembly 2212 is switched from the energy storage state to an energy release state, and the clip-lock panel 2211 is moved obliquely upward along the axial direction of the cylindrical protrusions 24 under the action of the elastic assembly 2212, until the cylindrical protrusions 24 engage with the cylindrical slots 13, thereby powering the laser element and/or performing the adjustment of laser elements parameters.

Preferably, the button assembly 222 includes a release button 2221 arranged at the front panel of the housing 2 corresponding to the second accommodating space 23, and a frame connector 2222 arranged behind the release button 2221. A vertical strip-shaped slot 2221a is provided backside of the release button 2221, and an inclined strip-shaped slot 22112 is provided frontside of the clip-lock panel 2211. The vertical strip-shaped slot 2221a and the inclined strip-shaped slot 22112 have openings oriented perpendicular to left and right panels of the housing 2, respectively. An inclined direction of the inclined strip-shaped slot 22112 is perpendicular to the axis of the cylindrical protrusion 24. An upper rod 22221 and lower rod 22222 of the frame connector 2222 are respectively capable of sliding in the inclined strip-shaped slot 22112 and the vertical strip-shaped slot 2221*a*. A left rod 22223 and right rod 22224 of the frame connector 2222 are horizontally hinged to the left and right panels of the clamping box 223, respectively. When the release button 2221 moves backward, the vertical strip-shaped slot 2221*a* moves backward, which allows the lower rod 22222 of the frame connector 2222 rotating obliquely backward in the vertical strip-shaped slot 2221*a*, and in turn allows the upper rod 22221 of the frame connector 2222 rotating obliquely forward in the inclined strip-shaped slot 22112. At the same time, a force direction of the inclined strip-shaped slot 22112 is always the same as an inclination direction of the cylindrical protrusion 24, which allows the clip-lock panel 2211 to move downward along the inclination direction of the cylindrical projection 24.

Preferably, the clamping unit 22 further includes a buckle 26 disposed on the upper portion of the clip-lock panel 2211 and located in front of the cylindrical protrusion 24, and a buckle slot 14 is provided under the corresponding lower panel of the cartridge receiver 1 at a position corresponding to a position of the buckle. When the back panel of the cartridge receiver 1 is connected with the back panel of the housing 2, the buckle 26 exactly snaps into the buckle slot 14, and the male and female electrical interfaces inside the cylindrical protrusion 24 and the cylindrical slots 13 corresponding to the cylindrical protrusion are connected with each other, preventing the cartridge receiver 1 from slipping out of the housing 2 during use.

Preferably, an upper back portion of the cartridge receiver 1 is further provided with a heat sink 15 of the laser element. Preferably, a middle portion of the heat sink 15 is provided with a cooling inlet 151 for heat sink penetrating vertically, and the upper panel of the housing 2 is provided with a forced air cooling inlet 27 at a position corresponding to a position of the cooling inlet 151 for heat sink. The left panel and/or the right panel of the housing 2 are arranged with forced air cooling outlets 28, respectively, as shown in FIGS. 1-5. The heat sink 15 has a sheet-like multi-layer structure. An external active air-cooling device enters the air through the forced air cooling inlet 27, allowing the air to flow vertically and horizontally to the forced air cooling outlet 28 to perform forced wind cooling of the heat sink 15.

The front panel of the cartridge receiver 1 is provided with a display device or a warning light 18 to prompt completion of the connection after the laser element is ready for connection and to prompt that the laser is being outputted when the laser element is working.

Preferably, the cylindrical protrusions 24 are arrayed on the upper surface of the clip-lock panel 2211, and the cylindrical slots 13 are arrayed on the lower panel of the cartridge receiver 1, corresponding to the array of the cylindrical protrusions. Specifically, as shown in FIGS. 9-11, 18 cylindrical slots 13 are arrayed on the lower panel of the cartridge receiver 1 in two rows at an angle of 45° with the horizontal plane. Each of the cylindrical slots 13 is provided with an annular barrel-shaped metal ferrule, and the center of the metal ferrule has a cavity structure. In this example, the cavity has a diameter of 3 mm and a length of 5 mm, allowing the insertion of needle-like pins inside the cylindrical protrusion 24. Correspondingly, 18 cylindrical protrusions 24 are arrayed on the upper panel of the clip-lock panel in two rows at an angle of 45° with the horizontal plane. The cylindrical protrusions 24 are internally provided with electrical pins for matching the internal structure of the cylindrical slots 13. After the cartridge receiver 1 is inserted into the first accommodating space 21 of the housing 2, the cartridge receiver 1 is locked by the clamping unit 22; and when the lock state is released by pressing the release button 2221, the cartridge receiver 1 can be taken out from the first accommodating space 21.

When the cartridge receiver 1 is not inserted into the housing 2, the clip-lock panel 2211 and the cylindrical projections 24 are lifted under the action of the spring assembly 2212. As shown in FIG. 10, the back panel of the clip-lock panel 2211 is inclined, and the inclined back panel always has a portion in contact with an inclined side of the clamping box 223. The inclined surface has the same inclination angle as that of the axis of the cylindrical protrusion 24. When the cartridge receiver 1 is inserted, the release button 2221 is pressed, and the inclined panel of clip-lock panel 2211 is forced to move downward, while the cylindrical protrusion 24 and the electrical ferrule inside thereof are moved downward, so that the cartridge receiver 1 can be inserted. After the cartridge receiver is inserted to reach a certain depth, for example, the back panel of the cartridge receiver 1 abuts against to the back panel of the housing 2 or the back panel of the cartridge receiver 1 abuts against the positioning block disposed on the back panel of the housing 2, as shown in FIG. 11, the release button 2221 is released, the clip-lock panel 2211 is bounced, and the cylindrical protrusion 24 and the electrical ferrule inside thereof are inserted into the cylindrical slots 13 and the electrical ferrule, to realize the communication of the circuit. At the same time, the optical interfaces 12 are cooperated to achieve optical communication. Under the action of the elastic assembly 2212, such as a spring, the cartridge receiver 1 is subjected to a rearward force to press the electrical interface 11 and optical interfaces 12. In addition, under the restriction of the buckle 26, the cartridge receiver 1 cannot be loosened or accidentally taken out.

Example 3

Preferably, interiors of the cylindrical protrusions 24 and cylindrical slots 13 are respectively provided with male and female electrical interfaces that can match with each other. The cylindrical protrusions 24 pass upward through the clamping port 212 and snap into the cylindrical slots 13 under an action of the elastic assembly 2212, so as to power the laser element and assist in adjusting parameters of the laser element. Preferably, the electrical interfaces of cylindrical protrusions 24 are connected with a power supply and/or a parameter control device for adjusting the laser element through the electrical output joint 29 arranged on the housing 2. Electrical interfaces 11 of the cylindrical slots 13 are respectively directly connected to a port of the power supply inside the laser element and/or parameter control interfaces including an interface for adjusting power, an interface for adjusting wavelength, and an interface for adjusting a pulse.

One end of the electrical interface 11 is connected to the electrical interface of the laser unit, and the other end is connected to the electrical input joint 29 of the housing.

Preferably, a front portion of the left panel and the right panel of the cartridge receiver 1 is provided with an anti-slip groove structure 17, and the plugging port 211 further includes plugging cartridge receiver grooves 2111 for the cartridge receiver corresponding to the anti-slip groove structure 17 in front of the left panels and right panel of the housing 2. This is convenient for the use to remove the cartridge receiver 1 from the housing 2 by hand.

Example 4

An exchangeable laser array is provided. The exchangeable laser array includes at least two of the above-mentioned exchangeable laser units, and in each of exchangeable laser units, a left side and right side of the housing are respectively provided with a horizontal guide channel array and a horizontal guide rail army. A plurality of exchangeable laser units can be snap-fitted side-by-side through the horizontal guide channel array and horizontal guide rail array, and it is easy to disassemble and replace the exchangeable lasers. In addition, as a preferred solution, the housing 2 also has a forced air cooling outlet 28 at a position corresponding to the back panel of the heat sink.

The exchangeable laser array is composed of a plurality of exchangeable laser units that have uniform shape and uniform output interfaces and the housings 2 with the uniform optical fiber joints 25 and electronic joints. The optical fiber joints 25 of the housings 2 are directly or indirectly connected to external optical fibers, output lasers having multiple wavelengths through different optical fibers to different instruments such as photodynamic therapy devices or dedicated wavelength switchers 3. In particular, as shown in FIG. 12, there are 4 housings 2, and 2 cartridge receivers 1. According to the above manner, the exchangeable laser array of the disclosure can realize the quick and convenient disassembly and assembly of the cartridge receiver 1 (i.e., the laser element). The replacement of the laser element can achieve the switch of different output wavelengths. For example, if there is only a laser element with two emission wavelengths of 630 nm and 664 nm in the cartridge receiver, while Foscan photosensitizer is temporarily used for treatment (the treatment wavelength is 652 nm) during the treatment, then it will be only required to purchase a cartridge receiver with 652 nm emission wavelength, and insert it into a housing in vacant.

The electrical interface of each exchangeable laser unit of the exchangeable laser array can be connected to the power and control system of the photodynamic therapy device, and thus is powered and controlled by the photodynamic therapy device. The optical fiber output interface of the exchangeable laser array is connected to an external optical fiber. In this example, the array including four housings is connected with four external optical fibers. These external optical fibers can be directly connected with wavelength switchers to realize selective output of the wavelength, or respectively connected with different photodynamic therapy devices.

Wavelength switchers can be implemented in a variety of ways. For example, the output wavelength can be selected by coupling an all-in-one optical fiber coupler to one output optical fiber and controlling the output wavelength of the laser array, or multiple wavelengths can be multiplexed and selected through a wavelength division multiplexer (WDM). In addition, the coupling and switching of the plurality of optical fibers to one or more optical fibers can be controlled by mechanical motion.

Example 5

Figure 13:
FIG. 13 is a schematic diagram illustrating the mechanical coupling and switching principle in optical fibers between the exchangeable laser of the exchangeable laser array of the disclosure and the wavelength switcher of the disclosure.
Figure 14:
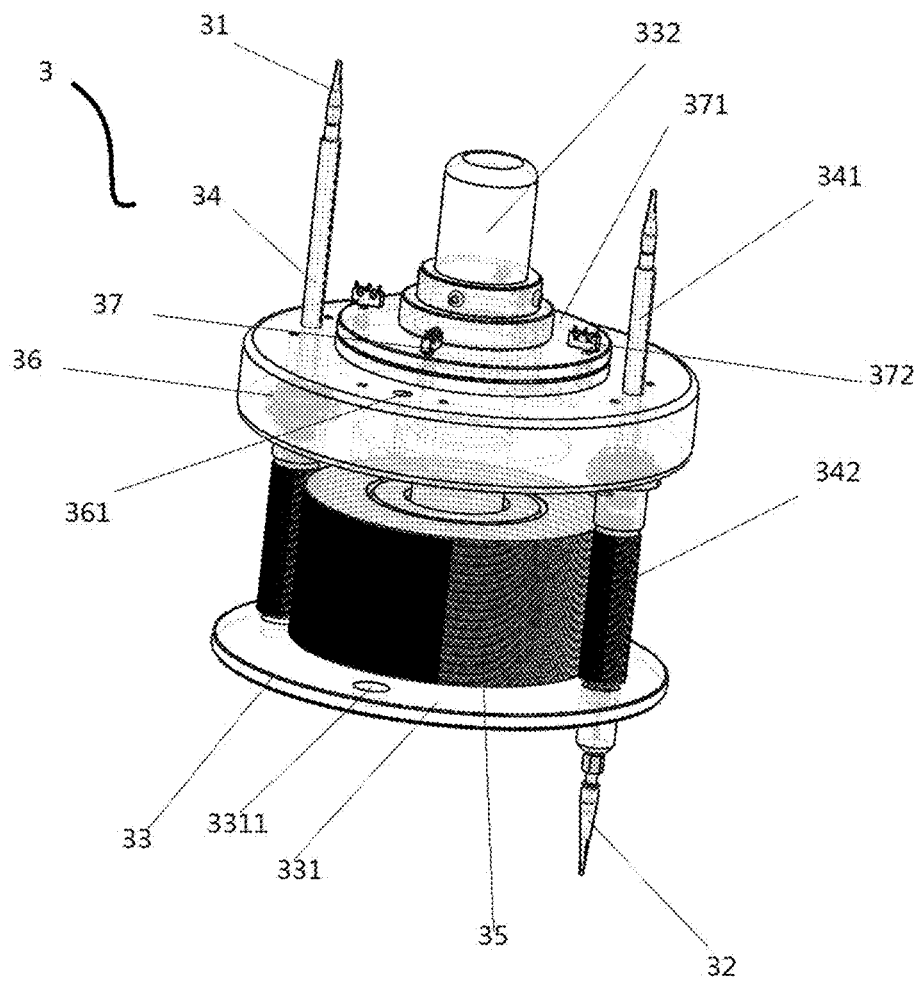
FIG. 14 is a three-dimensional schematic diagram illustrating the structure of the wavelength switcher of exchangeable laser array of the disclosure.
Figure 15:
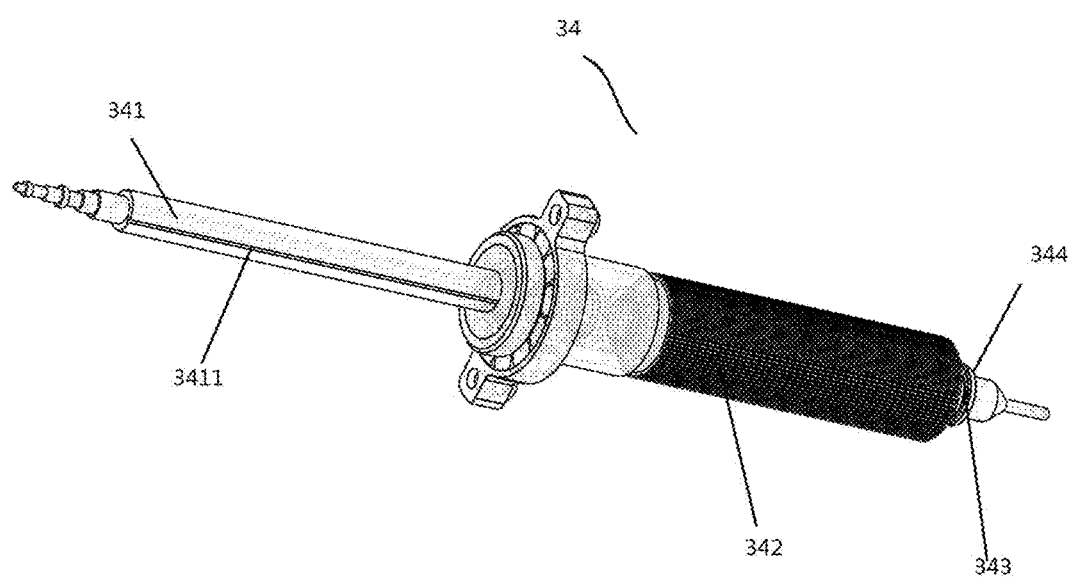
FIG. 15 is a three-dimensional schematic diagram illustrating the structure of the optical fiber plug of the exchangeable laser array of the disclosure.
Figure 16:
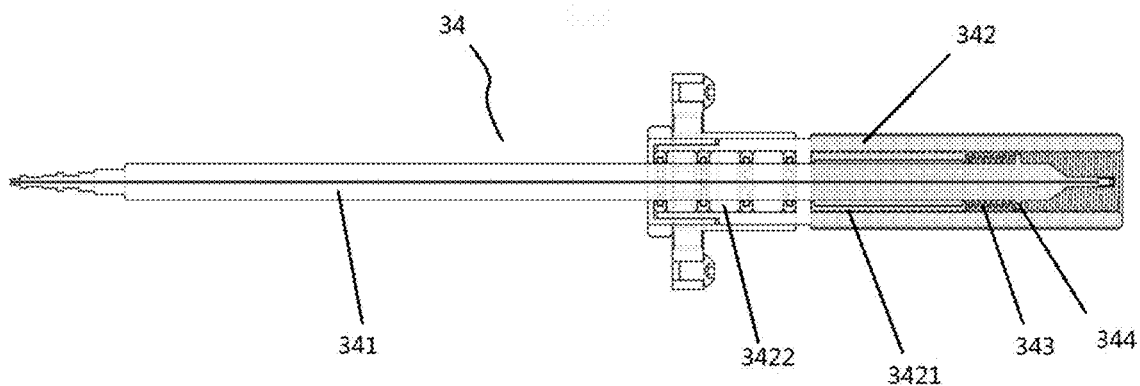
FIG. 16 is a cross-sectional schematic diagram illustrating the structure of the optical fiber plug of the exchangeable laser array of the disclosure, in which the optical fiber plugging rod is located at an extreme position.
Figure 17:
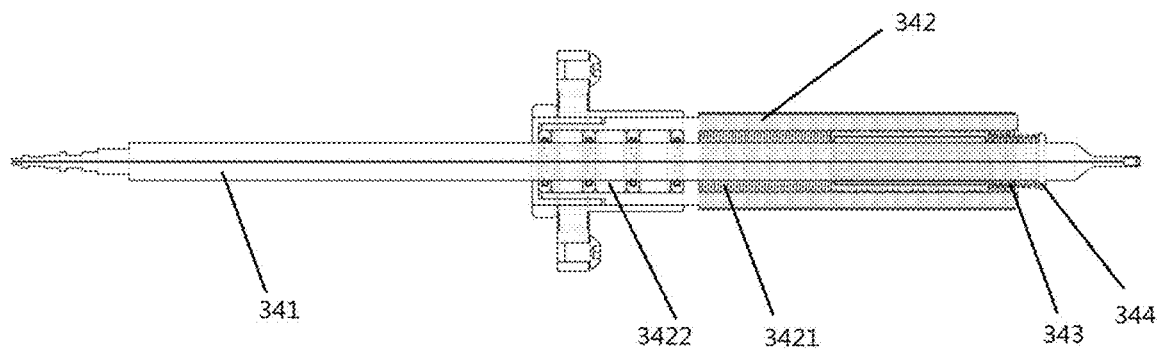
FIG. 17 is a cross-sectional schematic diagram illustrating the structure of the optical fiber plug of the exchangeable laser array of the disclosure, in which the optical fiber plugging rod is located at a plugging position.
Figure 18:
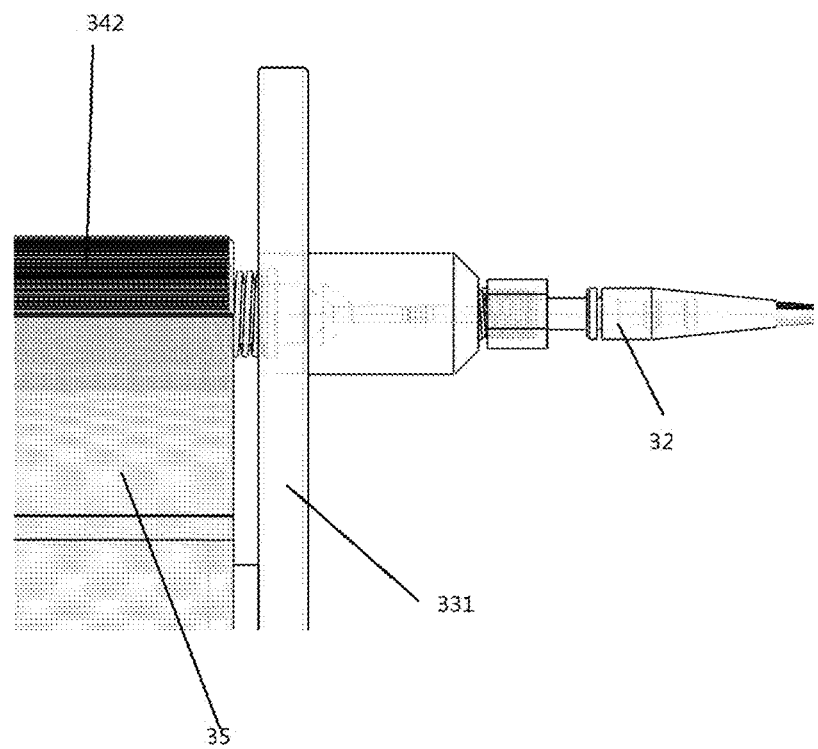
FIG. 18 is a partial diagram illustrating the structure that the optical fiber plugging rod is inserted into the optical fiber output interface, according to the exchangeable laser array of the disclosure.

FIG. 13 shows the principle of mechanical coupling and switching of optical fibers between the exchangeable laser array and the wavelength switcher. Through the relative positional change among the plurality of fiber optical plugs that are connected to the plurality of optical fiber input interfaces, and the optical fiber output interface, when a certain input optical fiber is aligned with the optical fiber output interface, laser in the optical fiber connected to this optical fiber plug is output, so as to realize switching of different wavelength outputs.

To ensure the efficiency of optical fiber coupling, it is required the precise alignment effect among the optical fiber plugs and optical fiber output interfaces. In order to achieve this effect, it is necessary to optimize the simple displacement motion into a cyclic motion of displacement-insertion-extraction-displacement, or to simulate the action of manually inserting a optical fiber interface by mechanical automatic motion. In order to achieve the above complex motions, the present disclosure adopts the following scheme.

The wavelength switcher 3, as shown in FIGS. 14-20, includes a plurality of optical fiber input interfaces 31 connected (directly or indirectly) to optical joints 25 of exchangeable laser units of the exchangeable laser array, one optical fiber output interface 32, a base 33 and a plurality of optical fiber plugs 34. The base 33 includes a baseplate 331 and a stationary shaft 332 extending upward along a center of the baseplate 331. The stationary shaft 332 is fixed with a drive gear 35 and an optical fiber displacement disk 36 that coincide with an axis of the stationary shaft 332 from bottom to top. The base 33 is not rotatable and movable, and is a center where the wavelength switcher 3 is fixed to the other peripheral devices. Preferably, a bearing is provided between the drive gear 35 and/or the fiber displacement disk 36 and the stationary shaft 332.

The optical fiber plugs 34 include optical fiber plugging rods 341, a driven gear 342 disposed at a periphery of the optical fiber plugging rods 341 and meshing with the drive gear 35. The optical fiber insertion rod 342 is provided with an optical fiber at an axial position thereof. One end of the optical fiber plugging rod 342 is connected to the optical fiber input interface 31, and other end of the optical fiber plugging rod is connected to the optical fiber output interface 32; and vice versa.

Preferably, the optical fiber plugs 34 are uniformly or axisymmetrically disposed on the optical fiber displacement disk 36 at a radial periphery of the drive gear 35. Several output ports 3311 for spirally connecting the optical fiber output interfaces 32 are disposed on the baseplate 331 vertically corresponding to the optical fiber plugs 34. The optical fiber output interface 32 is provided with an external thread for spirally connecting the output ports 3311, adaptively.

Several optical fiber plugging ports 361 for positioning the optical fiber plugs 34 are disposed on the optical fiber displacement disk 36 at a radial periphery of the drive gear 35.

When the optical fiber plugging rods 341 are located above the baseplate 331, the optical fiber displacement disk 36 is rotated under an action of the drive gear 35 and driven gear 342, and thus the optical fiber plugs 34 are rotated about the axis of the stationary shaft 332; when the optical fiber plugging rods 341 are rotated about the axis of the stationary shaft 332 and are rotated above the output ports 3311, the optical fiber plugging rods 341 are moved up or down along the optical fiber plugging ports 361 under the action of the drive gear 35 and driven gear 342, so as to pull out from the output ports 3311 or insert into the optical fiber output interfaces 32.

A large drive gear 35 and a small driven gear 342 are used to form a main transmission structure, and the optical fiber plugs 34 are disposed at a center of the small driven gear 342. When the central shaft of the driven gear 342 is unmovable, the rotation of the drive gear 35 drives the driven gear 342 to rotate, and the rotation of driven gear 342 drives the optical fiber insertion rod 341 to move up and down, thereby completing a insertion-extraction operation of the optical fiber insertion rod 341. When the central shaft of the driven gear 342 is movable, i.e., when the optical fiber plugging rod 341 is completely above the baseplate 331, the driven gear 35 is locked with the optical fiber plug 34 and thus they both cannot be rotated about their own axis, the driven gear 342 drives the fiber displacement plate 36 to rotate along the drive gear 35 under the action of the drive gear 35, thereby realizing the rotational translation of the optical fiber plugs 34.

Figure 19:
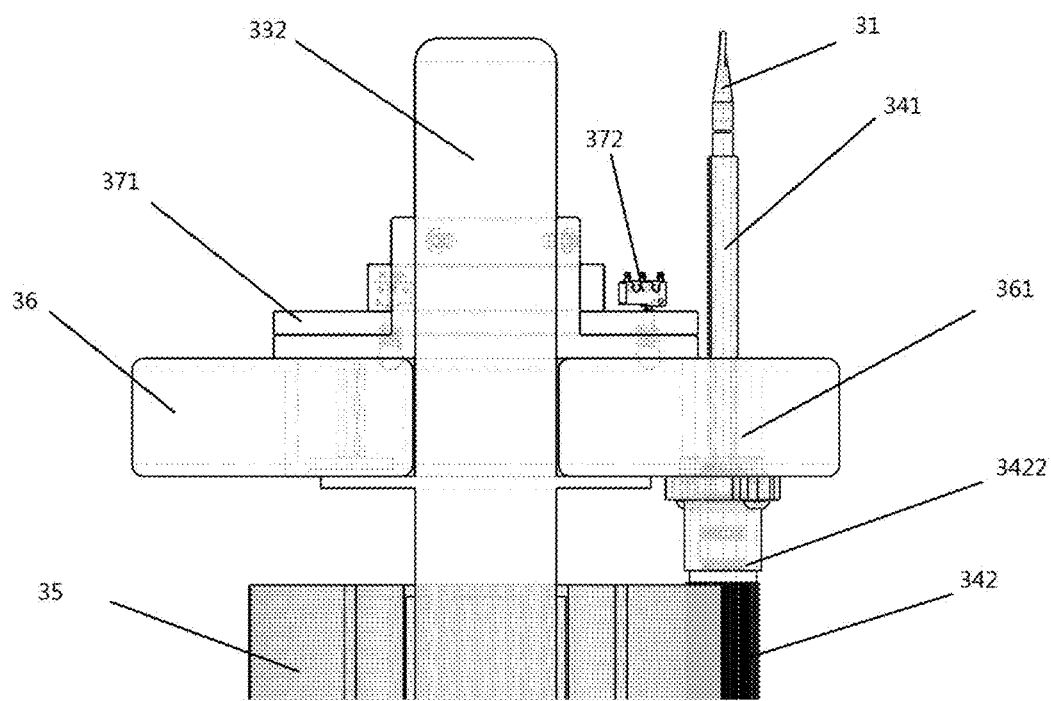
FIG. 19 is a schematic diagram illustrating the structures of the optical fiber displacement disk and micro-switch device, according to the exchangeable laser array of the disclosure.
Figure 20:
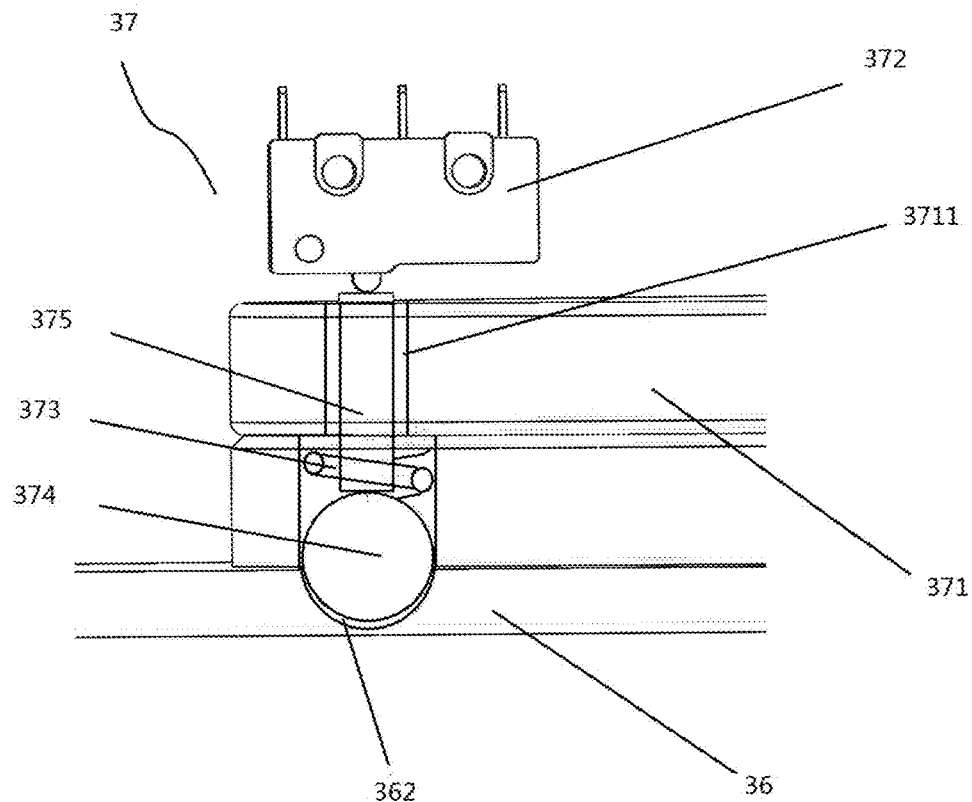
FIG. 20 is a perspective structural diagram of the micro-switch device according to the exchangeable laser array of the disclosure.

Preferably, as shown in FIGS. 19-20, the wavelength switcher 3 further includes a micro-switch device 37 disposed above the optical fiber displacement disk 36. The micro-switch device 37 includes a micro-switchgear 371, a plurality of micro-switch elements 372, a micro-motion spring 373, a limiting ball 374 and a micro-motion rod 375. The micro-switchgear 371 is provided with micro-slots 3711. The micro-motion spring 373, limiting ball 374 and micro-motion rod 375 are disposed inside the micro-slots 3711. In addition, the micro-motion spring 373 is sleeved on the micro-motion rod 375, and one end of the micro-motion rod 375 abuts against the triggering part of the micro-switch element 372, and the other end abuts against the limiting ball 374. Micro-switch positioning slots 362 with the same angle as the optical fiber plugs 34 are disposed on the optical fiber displacement disk 36. When the optical fiber displacement disk 36 is rotated, the limiting ball 374 is moved from one micro-switch positioning slot 362 to an adjacent micro-switch positioning slots. At the same time, the optical fiber plug 34 is moved from an upper position of one output port 3311 to an upper position of an adjacent output port. Specifically, the optical fiber plugging ports 361 are axisymmetrically disposed on the optical fiber displacement disk 36, and micro-switch positioning slots 362 are adaptively disposed in a radial direction of the optical fiber displacement disk 36 in which the optical fiber plugging ports 361 are located, so as to ensure that the optical fiber plug 34 can be accurately positioned above the output ports 3311 when the optical fiber displacement disk 36 is rotated.

This structure has two main functions: 1. when the optical fiber plug 34 is aligned with the optical fiber output interface 32 of the baseplate 331 and is completely located above the baseplate 331, the limiting ball 374 is rolled into the micro-switch positioning slots 362 of optical fiber displacement disk 36 under the motion of the micro-motion spring 373. After that, the rotation of the optical fiber displacement disk 36 is stopped due to an increase in resistance. The rotation of the drive gear 35 causes the optical fiber plug 34 to rotate along its own axis, and causes the optical fiber plugging rod 341 to move downward until it is inserted into the optical fiber output interface 32 of the baseplate 331. 2. The drive gear 35 is backward rotated, so that the optical fiber plug 34 is driven away from the optical fiber output interface 32 and retracted to the uppermost position. After that, the rotational resistance of the driven gear 342 is increased, and thus the limiting ball 374 is forced to be disengaged from the micro-switch positioning slot 362 on the upper surface of the optical fiber displacement disk 36. Therefore, the optical fiber plug is driven by the drive gear 35 to be displaced to the next optical fiber output interface.

The limiting ball 374 is connected to the triggering unit of the micro-switch elements 372 via the micro-motion rod 375 and the micro-motion spring 373. When the limiting ball 374 is disengaged from the micro-switch positioning slot 362 of the optical fiber displacement disk 36, the position of the limiting ball rises, touching the micro-switch elements 372 to turn the switch on; when the limiting ball 374 enters the micro-switch positioning slot 362 of the optical fiber displacement disk 36, the position of limiting ball drops, and thus the micro switch element 372 will be turned off. According to the signal of the micro-switch elements 372, it can be determined whether or not the limiting ball 374 is in the micro-switch positioning slot 362, so as to control the rotation direction of the drive gear 35.

The wavelength switcher 3 can realize a coupling switching output of wavelength in which the plurality of optical fibers transmitting lase with different wavelength input, but one wavelength outputs by using the drive gear 353. When the input and output fiber interfaces are increased, it is only required to install more optical fiber plugs 34 and coupling optical fiber joints. This avoids the control complexity and the reduction of coupling precision caused by the use of multiple rotation and displacement control devices when the number of fiber interfaces increases. The output of the wavelength switcher 3 described above can be used not only with one output optical fiber, but also with two or more optical fiber outputs, the principle of which is similar to that of one optical fiber.

Preferably, the driven gear 342 is connected to the optical fiber plugging rods 341 through a screw-nut pair 3421. On the optical fiber plugging rods 341, lower portions of the optical fiber plugging rods 341 are provided with vertical positioning slots 3411 matching with positioning protrusions of the optical fiber plugging ports 361. The vertical positioning slots 3411 are locked with the positioning protrusions in the optical fiber plugging ports 361, so that the optical fiber plugging rods 341 do not rotate relative to the optical fiber displacement disk 36. A screw external thread matching with a screw internal thread of the driven gear is provided on the optical fiber plugging rods 341 below the vertical positioning slots 3411. When the driven gear 342 rotates, the optical fiber plugging rods 341 are pushed up and down by the screw-nut pair 3421.

Preferably, an optical fiber plugging rod bearing 3422 is provided between the driven gear 342 and the optical fiber plugging rods 341. The optical fiber plugging rod bearing 3422 is composed of at least two bearings capable of withstanding axial opposite forces. In this example, there are three optical fiber plugging rod bearings 3422, which ensures smooth rotation and smooth movement up and down.

The drive gear 35 may be disposed between, above or below the baseplate 33 and the optical fiber displacement disk 36, and the position thereof may be flexibly adjusted as needed.

Preferably, a lower portion of the screw internal thread is provided with a spring 343 and a spring positioning shoulder 344. Preferably, below the spring positioning shoulder 344 is an optical fiber ferrule connected to the optical fiber output interface 32.

The arrangement of the spring 343 and the spring positioning shoulder 344 enable the optical fiber plugging rod 341 to be elastically inserted into the optical fiber output interface 32, avoiding the damage of head portion of the optical fiber ferrules at the bottom. In addition, there is a downward force after insertion, so that the coupling between the fiber ferrules is tight enough without loosening.

Preferably, the screw internal thread of the driven gear 342 is longer than the screw external thread of the optical fiber plugging rod 341. When a top of the screw external thread abuts against a top of the screw internal thread, and/or when a bottom of the vertical positioning slot 3411 abuts against the bottom of the vertical positioning protrusion of the optical fiber plugging port 361, The bottom of the optical fiber plugging rod 341 is located at least completely above the baseplate 331, so that the optical fiber plugging rod 341 is retracted from the optical fiber output interface 32 under the action of drive gear and driven gear, and is retracted to such as an extreme positon shown in FIG. 16. The screw external thread reaches the upper end of the screw internal thread, and/or the positioning protrusion of the optical fiber plugging port 361 reaches the bottom of the vertical positioning slot 3411 on the fiber plugging rod 341, so that the driven gear 342 will not be able to rotate along its own axis, which drives the fiber displacement plate 36 to rotate. The extreme position of the optical fiber plugging rod 341 is defined at where the screw external thread reaches the upper end of the screw internal thread, and/or the positioning protrusion of the optical fiber plugging port 361 reaches the bottom of the vertical positioning slot 3411 on the fiber plugging rod 341. The docking position of the fiber plugging rod 341 and the optical fiber output interface 32 is accurately positioned by the number of turns of the drive gear 35 in the reverse direction.

Figure 21:
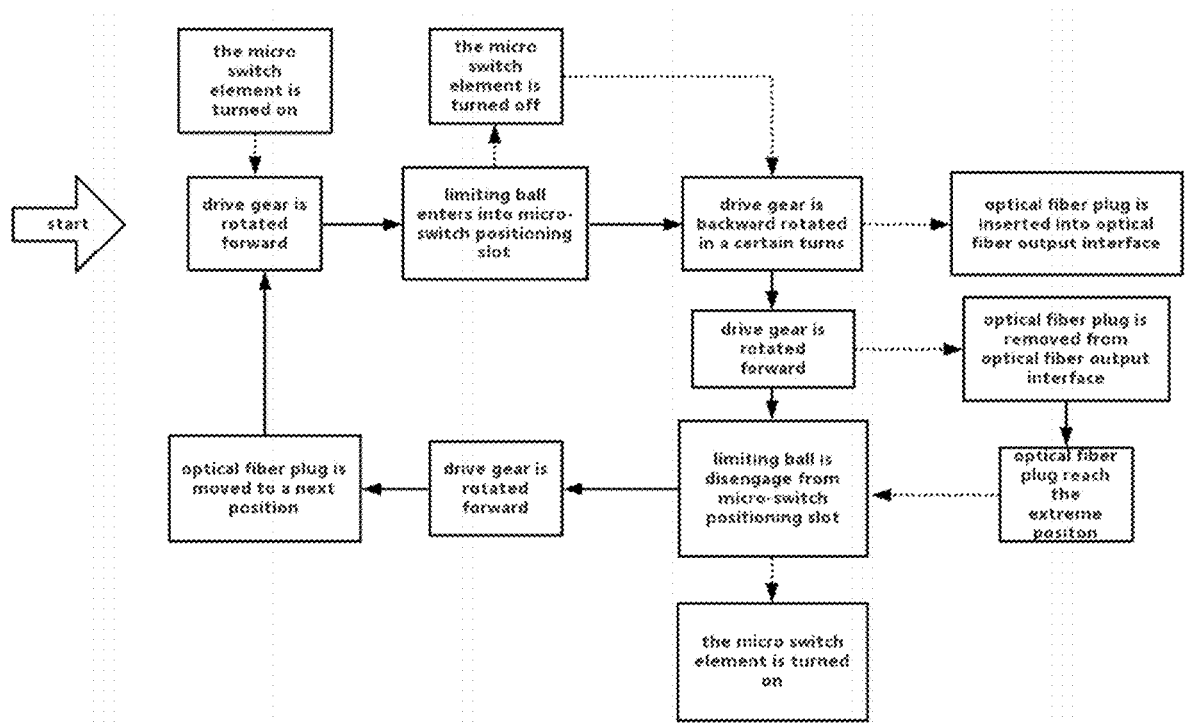
FIG. 21 is a flow chart showing the operation of the wavelength switcher according to the exchangeable laser array of the disclosure.

The flowchart of the disclosure is shown in FIG. 21.

Before the start state, the optical fiber plugging rod 341 is completely located above the baseplate, and the screw external thread reaches the upper end of the screw internal thread and/or the positioning protrusion of the fiber plugging port 361 reaches the bottom of the vertical positioning slot 3411 on the fiber plugging rod 341. That is, the optical fiber plugging rod 341 is positioned at the extreme position (i.e., the optical fiber plugging rod 341 is pulled out to the extreme position in the upward direction), the limiting ball 374 is located in the micro-switch positioning slot 362.

In the first stage, the rotation of the optical fiber displacement disk 36 drives the optical fiber plug 34 to move from the current optical fiber output interface 32 to the next optical fiber output interface. Specifically, the drive gear 35 is controlled to rotate in the forward direction, which drives the optical fiber displacement disk 36 to rotate, removes the limiting ball 374 from the micro-switch positioning slot 362, and thus turns on the micro-switch element 374. The limiting ball 374 is snapped into the next micro-switch positioning slot of the optical fiber displacement disk 36 under the rotation of the optical fiber displacement disk 36, and the micro-switch element 374 is turned off. The turning on or off of the micro-switch element controls the backward rotation of drive gear 35.

In the second stage, the optical fiber plugging rod 341 of the optical fiber plug 34 is moved downwardly to dock with the optical fiber output interface 32. Specifically, the drive gear 35 is backward rotated, and rotated in a certain turns, which drives the optical fiber plugging rod 341 to move downwardly to the optical fiber output interface 32 and laser-coupled output to the photodynamic therapy device for photodynamic therapy.

In the third stage, the optical fiber plugging rod 341 of the optical fiber plug 34 is moved upwardly to the extreme position. Specifically, when the treatment is completed, the drive gear 35 is controlled to rotate in the forward direction, and the optical fiber plugging rod 341 is moved upwardly and gradually removed from the optical fiber output interface 32, is finally moved to the position before the start state described above, so as to complete a use period.

The control of the forward rotation of the drive gear may be performed by a control system provided in the wavelength switcher 3, or may be performed by the photodynamic therapy device. Specifically, a start switch may be provided on the control system manipulation interface of the wavelength switcher 3 or on the control interface of the photodynamic therapy device. The drive gear is converted from forward rotation to forward rotation during a complete turning on and off of the micro-switch element 37.

It should be noted that the above description is only intended to enable those skilled in the art to more fully understand the present disclosure without limiting the present discourse in any way. It should be appreciated that various modifications and changes can be made to the present disclosure, although the present disclosure has been described above and illustrated in the accompanying drawings. Any modifications, equivalents, improvements, etc. made within the spirit and scope of the present disclosure are intended to be included within the scope of the present disclosure.

What is claimed is:

1. An exchangeable laser unit, comprising: laser elements, wherein the exchangeable laser unit further comprises cartridge receivers for fixing the laser elements and housings for clamping the cartridge receivers; the cartridge receivers have a same shape and optical interfaces;

each of the optical interfaces comprises a tapered cavity with a cone top at a front of each of the optical interfaces and an axis extending horizontally rearward from each of the optical interfaces; a small cylindrical cavity is arranged extending horizontally forward from the cone top of the tapered cavity and is in communication with the tapered cavity; a big cylindrical cavity is arranged extending horizontally backward from a cone bottom of the tapered cavity, a front side of the small cylindrical cavity is directly connected to a laser output of the laser element, or connected to a laser output of the laser element through an optical fiber ferrule;

a back panel of each of the housings is provided with an optical joint capable of matching with each of the optical interfaces of the cartridge receiver, and the optical joint comprises a tapered adapter having a same shape as the tapered cavity, and an external optical fiber disposed along a longitudinal axis position of the tapered adapter; a front end of the external optical fiber is provided with an external optical fiber ferrule capable of inserting into the small cylindrical cavity; the external optical fiber ferrule is arranged at a front end of the tapered adapter; a cylindrical adapter with a same shape as the large cylindrical cavity is arranged extending forward from a back end of the tapered adapter; the cylindrical adapter extends to be flush with the back panel of each of the housings;

each of the housings comprises a first accommodating space for accommodating the cartridge receiver; a front panel of each of the housings is provided with an insertion port for a horizontal insertion of the cartridge receiver into the first accommodating space; the first accommodating space and the cartridge receiver have a same shape;

a left panel and a right panel of the cartridge receiver are provided with horizontal positioning grooves, and a left panel and a right panel of the first accommodating space cartridge receiver are provided correspondingly with horizontal positioning protrusions;

each of the housings further comprises a clamping unit and a second accommodating space for accommodating the clamping unit; wherein the second accommodating space is disposed under the first accommodating space and is in communication with the first accommodating space through a clamping port provided on a bottom panel of the first accommodating space; the clamping unit comprises a clip-lock assembly, and the clip-lock assembly comprises a clip-lock panel disposed horizontally and an elastic assembly disposed under the clip-lock panel;

the clamping unit further comprises a clamping box, and the clamping box is fixed to the second accommodating space; a lower portion of the elastic assembly is fixed to a bottom of the clamping box; a left side and a right side of the clamping box are provided with a plurality of backwardly inclined upper-lower guide rails, and a left and a right side of the clip-lock panel are correspondingly provided with a plurality of backwardly inclined upper-lower guide channels;

wherein the clip-lock panel is moved upward under an action of the elastic assembly, and an upper and a lower position of each of the optical interfaces are accurately positioned, so that the external optical fiber ferrule is accurately docked with the small cylindrical cavity when the cartridge receiver is pushed into the first accommodating space;

the tapered cavity has a taper angle of 45°; the clamping unit further comprises a button assembly, and the button assembly comprises a release button arranged at the front panel of each of the housings corresponding to the second accommodating space and a frame connector arranged behind the release button;

a vertical strip-shaped slot is provided on a backside of the release button, and an inclined strip-shaped slot is provided on a frontside of the clip-lock panel; the vertical strip-shaped slot and the inclined strip-shaped slot have openings oriented perpendicular to the left and right panel of each of the housings; an inclined direction of the inclined strip-shaped slot is perpendicular to an inclination direction of the backwardly inclined upper-lower guide rails;

an upper rod and lower rod of the frame connector respectively slide in the inclined strip-shaped slot and the vertical strip-shaped slot; a left rod and right rod of the frame connector are horizontally hinged to a left and right panel of the clamping box, respectively; and the clip-lock panel further comprises a buckle disposed on an upper portion of the clip-lock panel and located behind of the inclined strip-shaped slot, and a buckle slot is provided under the lower panel of the cartridge receiver at a position corresponding to a position of the buckle.

2. The exchangeable laser unit according to claim 1, wherein a top portion of the optical fiber ferrule has a lens; when each of the optical interfaces is docked with the optical joint, a distance between a front end face of an optical fiber of the external optical fiber ferrule and the lens is equal to a focal length of the lens.

3. The exchangeable laser unit according to claim 2, wherein the lens is a convex lens or a lenticular lens or a graded-index lens.

4. The exchangeable laser unit according to claim 1, wherein an upper panel of the clip-lock panel is provided with a plurality of cylindrical protrusions with axes inclined rearward, and a lower panel of the cartridge receiver is correspondingly provided with a plurality of cylindrical slots having a same shape as the cylindrical protrusions;

when the buckle is engaged with the buckle slot, the cylindrical protrusions pass upward through the clamping port and snap into the cylindrical slots under an action of the elastic assembly.

5. The exchangeable laser unit according to claim 4, wherein male and female electrical interfaces are respectively provided inside the cylindrical protrusions and the cylindrical slots.

6. The exchangeable laser unit according to claim 4, wherein the cylindrical protrusions are arrayed on the upper portion of the clip-lock panel, and the cylindrical slots are arrayed on the lower panel of the cartridge receiver corresponding to the array of the cylindrical protrusions;

the backwardly inclined upper-lower guide rails have a inclined angle of 45°.

7. The exchangeable laser unit according to claim 1, wherein an upper back portion of the cartridge receiver is further provided with a heat sink, and an upper panel of each of the housings is provided with a forced air cooling inlet at a position corresponding to a position of the heat sink; the left panel and/or the right panel of each of the housings are arranged with forced air cooling outlets, respectively.

8. The exchangeable laser unit according to claim 7, wherein front portions of the left panel and the right panel of the cartridge receiver are provided with an anti-slip groove structure; the insertion port further comprises a plugging cartridge receiver groove corresponding to the anti-slip groove structure in front of the left panel and right panel of each of the housings.

9. An exchangeable laser array, comprising at least two of the exchangeable laser units according to claim 1, wherein in each of exchangeable laser units, a left side and right side of each of the housings are respectively provided with a horizontal guide channel array and a horizontal guide rail array.

* * * * *